United States Patent
Gremyachinskiy et al.

(10) Patent No.: US 11,001,611 B2
(45) Date of Patent: May 11, 2021

(54) SITE-SPECIFIC BIO-CONJUGATION METHODS AND COMPOSITIONS USEFUL FOR NANOPORE SYSTEMS

(71) Applicant: Roche Sequencing Solutions, Inc., Pleasanton, CA (US)

(72) Inventors: Dmitriy Gremyachinskiy, San Francisco, CA (US); Christos Tzitzilonis, Redwood City, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/134,179

(22) Filed: Sep. 18, 2018

(65) Prior Publication Data

US 2019/0002509 A1    Jan. 3, 2019

Related U.S. Application Data

(63) Continuation of application No. PCT/EP2017/057002, filed on Mar. 23, 2017.

(60) Provisional application No. 62/313,086, filed on Mar. 24, 2016.

(51) Int. Cl.

| | | |
|---|---|---|
| *C07K 14/315* | (2006.01) | |
| *C07K 1/107* | (2006.01) | |
| *C12Q 1/68* | (2018.01) | |
| *A61K 47/64* | (2017.01) | |
| *C07K 19/00* | (2006.01) | |
| *C12N 9/12* | (2006.01) | |
| *C12N 9/52* | (2006.01) | |
| *C12N 15/62* | (2006.01) | |

(52) U.S. Cl.
CPC .......... *C07K 14/315* (2013.01); *A61K 47/64* (2017.08); *A61K 47/6415* (2017.08); *C07K 1/1072* (2013.01); *C07K 1/1077* (2013.01); *C07K 19/00* (2013.01); *C12N 9/1205* (2013.01); *C12N 9/1241* (2013.01); *C12N 9/52* (2013.01); *C12N 15/62* (2013.01); *C12Q 1/68* (2013.01); *C07K 2319/03* (2013.01); *C07K 2319/20* (2013.01); *C12Y 207/07* (2013.01)

(58) Field of Classification Search
None
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,267,872 B1 | 7/2001 | Akeson et al. |
| 6,362,002 B1 | 3/2002 | Denison et al. |
| 6,464,842 B1 | 10/2002 | Golovchenko et al. |
| 6,617,113 B2 | 9/2003 | Deamer |
| 6,627,067 B1 | 9/2003 | Branton et al. |
| 6,673,615 B2 | 1/2004 | Denison et al. |
| 6,746,594 B2 | 6/2004 | Akeson et al. |
| 7,005,264 B2 | 2/2006 | Su |
| 7,846,738 B2 | 12/2010 | Golovchenko et al. |
| 2003/0104428 A1 | 6/2003 | Branton et al. |
| 2004/0121525 A1 | 6/2004 | Chopra et al. |
| 2013/0244340 A1 | 9/2013 | Davis |
| 2013/0264207 A1 | 10/2013 | Ju et al. |
| 2014/0134616 A1 | 5/2014 | Davis et al. |
| 2014/0249296 A1* | 9/2014 | Ploegh ................ C07K 1/107 530/387.3 |

FOREIGN PATENT DOCUMENTS

| | | |
|---|---|---|
| WO | 2015148402 | 10/2015 |
| WO | 2016144973 | 9/2016 |

OTHER PUBLICATIONS

Lim et al. "Site-specific albumination of a therapeutic protein with multi-subunit to prolong activity in vivo" J. Controlled Release 207: 93-100. (Year: 2015).*
Kasaraneni et al. "Retargeting Lentiviruses via SpyCatcher-SpyTag Chemistry for Gene Delivery into Specific Cell Types" mBio 8: e01860-17. (Year: 2017).*
International Search Report and Written Opinion from PCT/EP2017/057002, dated Jun. 12, 2017 (11 pages).
Dawson et al., "Synthesis of proteins by native chemical ligation," Science, 1994, vol. 266, pp. 776-779.
Li et al. "Structural analysis and optimization of the covalent association between SpyCatcher and a peptide Tag," J. Mol. Biol.; Jan. 23, 2014; vol. 426; Issue 2; pp. 309-317.
Shin et al. "Fmoc-Based Synthesis of Peptide-α-Thioesters: Application to the Total Chemical Synthesis of a Glycoprotein by Native Chemical Ligation," J. Am. Chem. Soc., 1999, vol. 121, pp. 11684-11689.
Zakeri and Howarth, "Spontaneous Intermolecular Amide Bond Formation between Side Chains for Irreversible Peptide Targeting," J. Am. Chem. Soc., 2010, vol. 132, pp. 4526-4527.

* cited by examiner

*Primary Examiner* — Sudhakar Katakam
*Assistant Examiner* — Zachary J Miknis
(74) *Attorney, Agent, or Firm* — FisherBroyles, LLP; Victoria L. Boyd; Adam Kurt Whiting

(57) ABSTRACT

The present disclosure relates to relates methods and associated compositions that provide fast, efficient site-selective conjugation of a protein, such as the pore-forming protein α-hemolysin, to a biomolecule, such as a DNA polymerase, and the use of such site-selective protein-biomolecule conjugates in nanopore devices and methods.

9 Claims, 2 Drawing Sheets

Specification includes a Sequence Listing.

SITE-SPECIFIC BIO-CONJUGATION METHODS AND COMPOSITIONS USEFUL FOR NANOPORE SYSTEMS

CROSS-REFERENCE TO RELATED APPLICATIONS

This is a continuation of International Application No. PCT/EP2017/057002, filed Mar. 23, 2017, and claims the benefit of U.S. Provisional Application No. U.S. 62/313,086, filed Mar. 24, 2016, the content of each of which is incorporated by reference in its entirety.

SEQUENCE LISTING INCORPORATION BY REFERENCE

This application hereby incorporates-by-reference a sequence listing submitted herewith in a computer-readable format, having a file name of "04338_526US1_SeqListing.txt" created on Sep. 17, 2018, which is 26,320 bytes in size.

BACKGROUND

A. Field

The present disclosure relates to fast, efficient chemical reactions for conjugating proteins, such as the pore-forming protein, α-hemolysin, to biomolecules, such as antibodies, receptors, and enzymes, such as DNA polymerase.

B. Description of Related Art

Single-molecule sequencing-by-synthesis (SBS) techniques using nanopores have been developed. See e.g., US Pat. Publ. Nos. 2013/0244340 A1 and 2013/0264207 A1. Nanopore SBS involves the use of a polymerase synthesize a DNA strand complementary to a target sequence template and determine the identity of each nucleotide monomer as it is added to the growing strand, thereby determining the target sequence. Each added nucleotide monomer is detected via a nanopore located adjacent to the polymerase active site and the growing strand. Obtaining an accurate signal requires proper positioning of a polymerase active site near a nanopore. Proper positioning typically is achieved by covalently linking the polymerase to the pore-protein that makes up the nanopore.

Monomeric pore-forming proteins have molecular weights range from as little as 5 kDa to 80 kDa, and these monomers form large multimeric complexes of 6, 7, 8, 9, 10, or more monomers, having molecular weights of 160, kDa, 180 kDa, 200 kDa, 220 kDa, or more. Under suitable conditions these multimeric complexes spontaneously form pores through lipid bilayer membranes. The well-studied pore-forming protein from S. aureus, α-hemolysin (α-HL) has a monomer molecular weight of 33 kDa and spontaneously forms a heptameric pore complex having a molecular weight of 231 kDa. Polymerases are large proteins that range in molecular weight from about 60 kDa to 100 kDa and even much larger multimeric complexes in some cases (e.g., RNA polymerase ~400 kDa multimer). The Klenow fragment of DNA polymerase I has a molecular weight of 68 kDa.

Accordingly, the kinetics of any reaction to conjugate these pore-forming proteins, like the α-hemolysin heptamer, to large biomolecules, like DNA polymerase, in order to provide a nanopore sensor will be extremely limited by the low concentration achievable (and relative low amounts available) with such large macromolecules. The maximum solubility of such large proteins in aqueous solution typically is limited to approximately 0.1 to 10 mg/mL. Thus, the concentration of the two macromolecules in solution used for a conjugation reaction is limited to ~1 μM to 1000 μM. For example, the α-hemolysin protein pore consists of 7 identical subunits totaling about 235,000 molecular weight. Thus a solution of 10 mg/ml has a concentration of about 42 μM. This relatively low concentration range effectively limits viable conjugation chemistries to those having extremely fast, irreversible reaction rates.

WO2015/148402A1 describes tagged nucleotides useful for nanopore sequencing, and describes two methods for attaching α-hemolysin to a polymerase. One method involves using the SpyTag-SpyCatcher enzymatic conjugation reaction (see e.g., Zakeri and Howarth (2010).JACS 132:4526-7). In this method, a SpyTag peptide fragment is attached as a recombinant fusion to the C-terminus of an α-HL monomer, and a SpyCatcher protein fragment is attached as a recombinant fusion to the N-terminus of the Phi29 DNA polymerase. A second method involves using an inverse electron demand Diels-Alder (IEDDA) reaction between an α-HL modified with a trans-cyclooctene group and a polymerase modified with a 6-methyl-tetrazine group.

Native Chemical Ligation (NCL) originally was developed as a synthesis method that allowed extension of synthetic polypeptides by ligating polypeptide fragments while maintaining native peptide bonding structure. (see e.g., Dawson et al., "Synthesis of proteins by native chemical ligation," Science 1994, 266, 776-779) The stoichiometric efficiency and site-specificity of NCL make it useful for glycopeptide synthesis and other synthetic methods where it is important to retain native peptide bonding. (See e.g., Shin et al., "Fmoc-Based Synthesis of Peptide-α-Thioesters: Application to the Total Chemical Synthesis of a Glycoprotein by Native Chemical Ligation," J. Am. Chem. Soc. 1999, 121, 11684-11689.)

Due to the relatively low-concentrations of pore-protein and polymerase typically used in forming a nanopore detection system for SBS, it is critical that highly efficient and site-specific conjugation reactions are developed that allow strong, selective, covalent conjugation between these two relatively large protein complexes. It is also critical that the conjugation reactions allow for freedom in attachment site selection in order to optimize the positioning of the conjugated molecules for specific uses, such as nanopore sequencing, that require precise macromolecular orientation. Thus, there remains a need for faster and more efficient processes to conjugate protein complexes, such as nanopores, to other biomolecules, such as enzymes.

SUMMARY

The present disclosure provides methods for site-specific conjugation of a pore-forming protein and a biomolecule, and the compositions comprising modified pore-forming proteins, biomolecules, and conjugates arising from the use of the methods of preparation. Further, the disclosure provides nanopore systems and compositions comprising the conjugates, and associated uses, including use in nanopore sequencing.

The method for site-selective conjugation of a protein to a biomolecule as disclosed herein generally comprises steps (a)-(c) as follows:
(a) contacting, under suitable reaction conditions, a protein, wherein the protein comprises a thiol group, with a compound of formula (I)

$$A\text{-}L_4\text{-}X \tag{I}$$

wherein, A is a thiol reactive group; $L_A$ is a linker; and X is a click chemistry reactive group; and thereby forming a modified protein of formula (II)

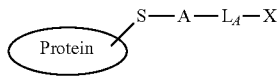
(II)

wherein S is a sulfur atom of the thiol group of the protein;
(b) contacting the modified protein of formula (ii) with a compound of formula (iii)

Y-L$_A$-B    (II)

wherein, B is a reactive group; $L_B$ is a linker; and Y is a click chemistry reactive group that undergoes a click chemistry reaction with the cognate click chemistry reactive group X of compound of formula (II); thereby forming a modified protein of structural formula (IV)

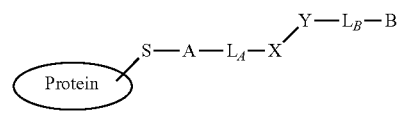
(IV)

and,
(c) contacting the modified protein of formula (IV), under suitable reaction conditions, with a biomolecule, wherein the biomolecule comprises a reactive group Z, wherein Z is capable of forming a covalent bond with the reactive group B, thereby forming the protein-biomolecule conjugate of formula (V)

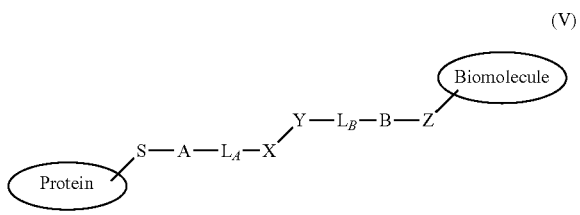
(V)

wherein, S is a sulfur atom of the thiol group of the protein; A is the thiol reactive group; $L_A$ is a linker; X is a click chemistry reactive group; Y is a click chemistry reactive group that undergoes a click chemistry reaction with the reactive group X; $L_B$ is a linker; B is a reactive group; and Z is a reactive group capable of forming a covalent bond with the reactive group B.

In some embodiments, the present disclosure also provides a composition comprising a modified pore-forming protein of structural formula (IVa)

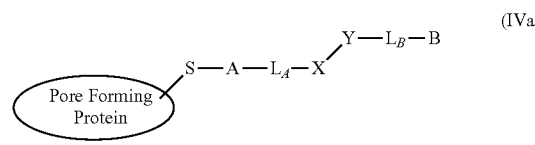
(IVa)

wherein, S is a sulfur atom of a thiol group of the pore forming protein; A is a thiol reactive group; $L_A$ is a linker; X is a click chemistry reactive group; Y is a click chemistry reactive group that undergoes a click chemistry reaction with the reactive group X; $L_B$ is a linker; and B is a reactive group.

In some embodiments, the present disclosure also provides a composition comprising a protein-biomolecule conjugate of formula (V)

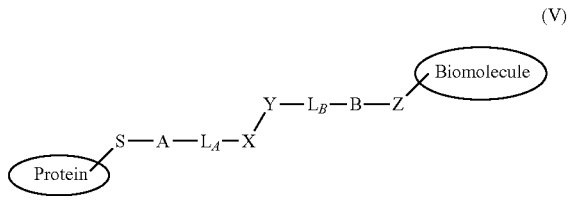
(V)

wherein, S is a sulfur atom of a thiol group of the protein; A is a thiol reactive group; $L_A$ is a linker; X is a click chemistry reactive group; Y is a click chemistry reactive group that undergoes a click chemistry reaction with the reactive group X; $L_B$ is a linker; B is a reactive group; and Z is a reactive group capable of forming a covalent bond with the reactive group B.

In embodiments of the site-selective conjugation methods and associated compositions disclosed herein, the reactive group B comprises a SpyTag peptide and the reactive group Z comprises a SpyCatcher protein. In some embodiments, wherein the SpyTag peptide comprises an amino acid sequence selected from AHIVMVDAYKPTK (SEQ ID NO: 1), AHIVMVDAYK (SEQ ID NO: 2), AHIVMVDA (SEQ ID NO: 3), and ahA-AHIVMVDAYKPTK (SEQ ID NO: 4). In some embodiments, the biomolecule comprising a reactive group Z is a fusion with a SpyCatcher protein, optionally wherein the SpyCatcher protein comprises an amino acid sequence of SEQ ID NO: 6, 7, or 8.

In some embodiments, the present disclosure further provides a nanopore composition comprising a protein-biomolecule conjugate of formula (V), wherein the protein is a pore-forming protein that is part of a nanopore. In some embodiments, the nanopore is embedded in a membrane, and optionally, the membrane can be attached to a solid substrate, and/or is formed such that it spans a well or depression or hole in a solid substrate, which optionally comprises a material selected from the group consisting of polymer, glass, silicon, and a combination thereof.

In some embodiments, the solid substrate further comprises adjacent to the nanopore a sensor, a sensing circuit, or an electrode coupled to a sensing circuit, optionally, a complementary metal-oxide semiconductor (CMOS), or field effect transistor (FET) circuit.

The disclosure also provides compounds and compositions that form as intermediates in the methods for site-selective conjugation of proteins to biomolecules, including the intermediate composition comprising a modified pore-forming protein of structural formula (IVa).

In embodiments of the site-selective conjugation methods and associated compositions disclosed herein, the protein is a pore-forming protein selected from the group consisting of α-hemolysin, β-hemolysin, γ-hemolysin, aerolysin, cytolysin, leukocidin, melittin, MspA porin, and porin A. In one embodiment, the pore-forming protein is α-hemolysin from *Staphylococcus aureus*. In one embodiment, the pore-forming protein is α-hemolysin C46 ("α-HL C46"), which comprises α-hemolysin from *S. aureus* with a K46C amino acid residue substitution. In some embodiments, the pore-forming protein is capable of forming a nanopore of diameter of about 0.5 nanometer to about 25 nanometers.

In some embodiments of the methods of preparation of the conjugate compositions of formula (I), the protein and/or the biomolecule are present in the reaction solution at a concentration of less than 1000 µM, 750 µM, 500 µM, 250 µM, 100 µM, 50 µM, 10 µM, 5µM, or 1 µM or less.

In embodiments of the site-selective conjugation methods and associated compositions disclosed herein, the protein is a pore-forming protein having a molecular weight of at least 20 kDa, 30 kDa, 40 kDa, 50 kDa, or greater. In some embodiments of the methods and compositions, the biomolecule has a molecular weight of at least 30 kDa, 40 kDa, 50 kDa, 60 kDa, 70 kDa, 80 kDa, or greater. In some embodiments, the pore-forming protein has a molecular weight of at least 30 kDa and the biomolecule has a molecular weight of at least 50 kDa.

In embodiments of the site-selective conjugation methods and associated compositions disclosed herein, the protein is a pore-forming protein that is a part of a multimeric complex, wherein the multimer is selected from hexamer, heptamer, octamer, nonamer, decamer, or larger multimer. In some embodiments, the protein is a pore-forming protein that is a single monomer which is part of a multmeric complex, wherein the other monomers of the complex do not comprise a conjugate composition of formula (V) (i.e., only a single monomer of the multimer is conjugated to the biomolecule).

In embodiments of the site-selective conjugation methods and associated compositions disclosed herein, the protein is pore-forming protein that is embedded in a membrane. In some embodiments, the protein is a pore-forming protein that is part of a nanopore. In some embodiments, the protein is attached to a solid substrate, and optionally the solid substrate comprises a material selected from the group consisting of polymer, glass, silicon, and a combination thereof.

In embodiments of the site-selective conjugation methods and associated compositions disclosed herein, the biomolecule is an enzyme capable of catalyzing the synthesis of a polymer. In some embodiments, the biomolecule is an enzyme selected from the group consisting of a DNA polymerase, RNA polymerase, reverse transcriptase, and DNA ligase. In some embodiments, the biomolecule is a naturally-occurring or non-naturally occurring (e.g., engineered) enzyme that has 5'→3' DNA polymerase activity and strong strand displacement activity but lacks 5'→3' exonuclease activity. In some embodiments, the biomolecule is a DNA polymerase, optionally selected from the group consisting of 9° N polymerase, *E. Coli* DNA Polymerase I, *E. Coli* DNA Polymerase II, Bacteriophage T4 DNA polymerase, Sequenase, Taq DNA polymerase, 9° N polymerase (exo-) A485L/Y409V, DNA polymerase Bst 2.0, and Phi29 DNA polymerase (φ29 DNA Polymerase). In some embodiments the biomolecule is DNA polymerase Pol6 comprising the amino acid of SEQ ID NO: 9. In some embodiments, the biomolecule comprising a reactive group Z is a fusion of a DNA polymerase Pol6 and a SpyCatcher protein, optionally the fusion comprising the amino acid sequence of SEQ ID NO: 10.

In some embodiments of the compositions and methods of preparation comprising a compound of formula (I), the linkers $L_A$ and $L_B$ comprise a covalently bonded chain of 2 to 100 atoms comprising one or more of the following chemical groups: linear ($C_1$-$C_5$) alkyl, linear ($C_1$-$C_5$) alkenyl, linear ($C_1$-$C_5$) alkynyl, ester, ether, amine, amide, imide, phosphodiester, and/or polyethylene glycol (PEG). In some embodiments, the linkers $L_A$ and $L_B$ attach to A and B either through a thioether bond to a sulfhydryl group on A and/or B, or through a peptide bond to a primary amine group of A and/or B. In some embodiments, the linkers $L_A$ and $L_B$ comprise a polymer of from 1 to 50 polyethylene glycol (PEG) moieties. In some embodiments of the compositions and methods of preparation comprising a compound of formula (I), the linkers $L_A$ and $L_B$ are independently selected from the group consisting of structures of formula (VIa)-formula (VIe).

DETAILED DESCRIPTION

Figure 1:
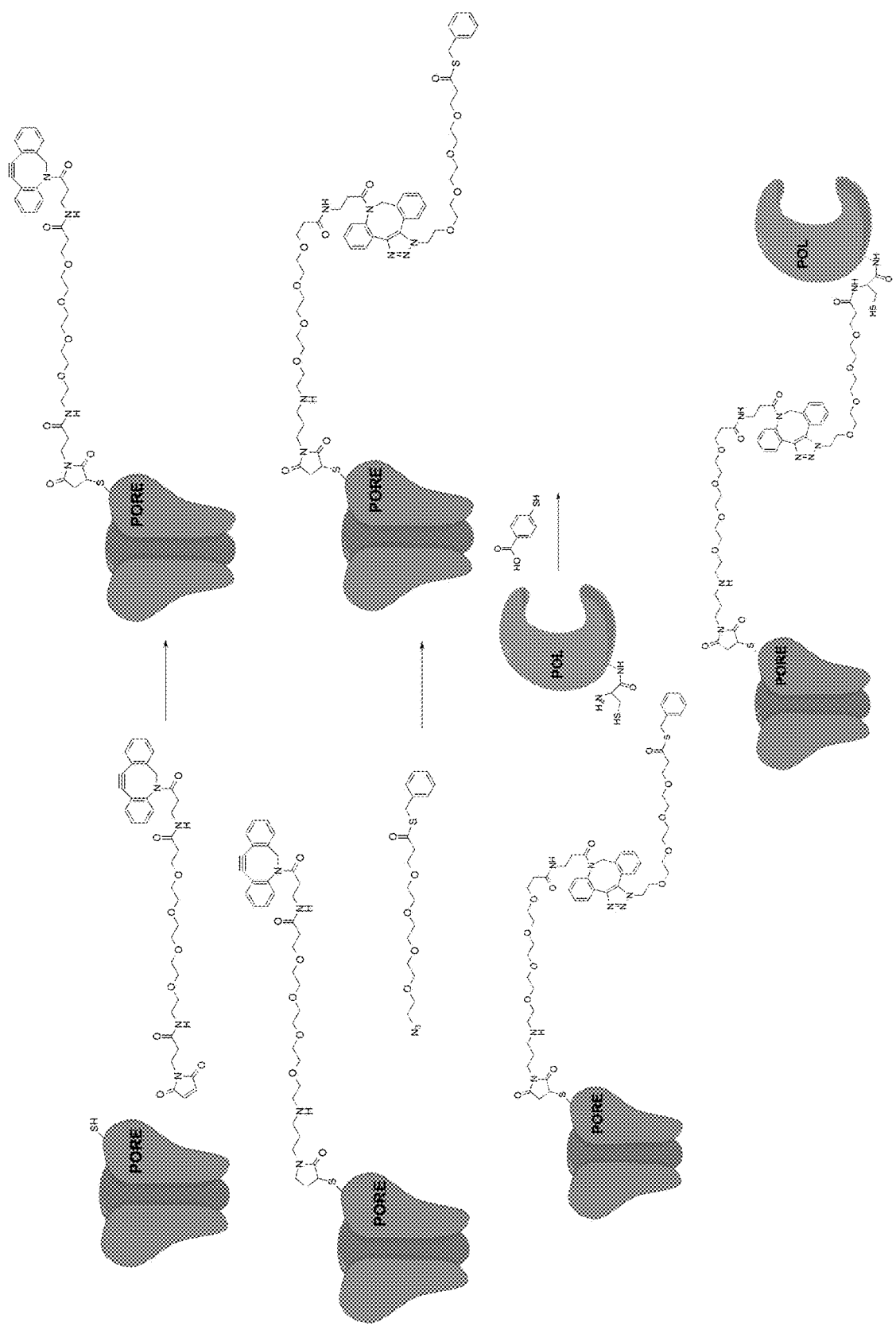
FIG. 1 depicts schematically (from top to bottom) the reaction steps and reagents use in an exemplary method of site-selective conjugation of a polymerase ("POL") to a nanopore ("PORE") via a combination of DBCO-azide click chemistry and a native chemical ligation (NCL) in accordance with the methods and compositions of the present disclosure. Exemplary materials and methods useful in the reactions depicted in FIG. 1 are detailed in Example 1 for the particular case of conjugating a α-HL heptameric nanopore complex to a Pol6 DNA polymerase.

The present disclosure is directed to methods for site-selective conjugation of proteins (e.g., the pore-forming protein, α-hemolysin) to other biomolecules (e.g., DNA polymerase oligonucleotides, antibodies and receptors) and the resulting protein-biomolecule conjugates of formula (V)

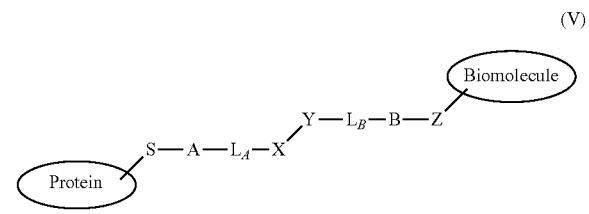

(V)

wherein, S is a sulfur atom of a thiol group of the protein; A is a thiol reactive group; $L_A$ is a linker; X is a click chemistry reactive group; Y is a click chemistry reactive group that undergoes a click chemistry reaction with the reactive group X; $L_B$ is a linker; B is a reactive group; and Z is a reactive group capable of forming a covalent bond with the reactive group B.

The present disclosure also provides compounds and compositions that form as intermediates in the methods for site-selective conjugation of proteins to biomolecules, including the intermediate composition comprising a modified pore-forming protein of structural formula (IVa)

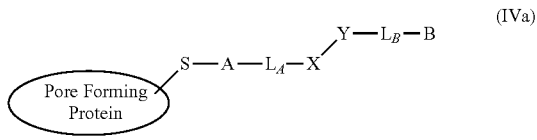
(IVa)

wherein, S is a sulfur atom of a thiol group of the pore forming protein; A is a thiol reactive group; $L_A$ is a linker; and X is a click chemistry reactive group; Y is a click chemistry reactive group that undergoes a click chemistry reaction with the reactive group X; $L_B$ is a linker; and B is a reactive group.

The method for site-selective conjugation of a protein to a biomolecule as disclosed herein generally comprises steps of:

(a) contacting, under suitable reaction conditions, a protein, wherein the protein comprises a thiol group, with a compound of formula (I)

(I)

wherein, A is a thiol reactive group; $L_A$ is a linker; and X is a click chemistry reactive group; and thereby forming a modified protein of formula (II)

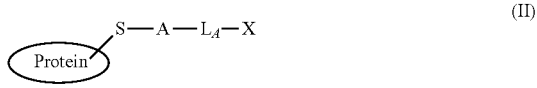
(II)

wherein S is a sulfur atom of a thiol group of the protein;

(b) contacting the modified protein of formula (ii) with a compound of formula (iii)

(III)

wherein, B is a reactive group; $L_B$ is a linker; and Y is a click chemistry reactive group that undergoes a click chemistry reaction with the cognate click chemistry reactive group X of compound of formula (II); thereby forming a modified protein of structural formula (IV)

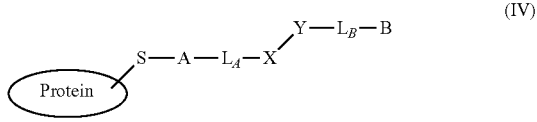
(IV)

and, (c) contacting the modified protein of formula (IV), under suitable reaction conditions, with a biomolecule, wherein the biomolecule comprises a reactive group Z, wherein Z is capable of forming a covalent bond with the reactive group B, thereby forming the protein-biomolecule conjugate of formula (V).

The disclosed methods, and compositions allow for fast, efficient conjugation between proteins and other biomolecules at relatively low concentrations and without large mole excesses of one reagent over the other. Accordingly, the compositions and chemical processes for preparing the conjugates disclosed herein are particularly well-suited for use in preparing nanopore compositions comprising a pore-forming protein embedded in a membrane covalently linked to a biomolecule, such as a DNA polymerase. Such nanopore compositions can be used in applications requiring nanopore detection, including single-molecule DNA sequencing-by-synthesis.

Further details of the compositions, methods, and parameters for use in the methods of site-selective conjugation of proteins to biomolecules are described herein below.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example "1 to 50" includes "2 to 25", "5 to 20", "25 to 50", "1 to 10", etc.

It is to be understood that both the foregoing general description, including the drawings, and the following detailed description are exemplary and explanatory only and are not restrictive of this disclosure.

Definitions

The technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.).

"Pore-forming protein," or "pore protein," as used herein refers to a natural or non-naturally occurring protein capable of forming a pore or channel structure in a barrier material such as a lipid bilayer or cell membrane. The terms as used herein are intended to include both a pore-forming protein in solution, and a pore-forming protein embedded in a membrane or barrier material, or immobilized on a solid substrate or support. The terms as used herein are intended to including pore-forming proteins as monomers and also as any multimeric forms into which they are capable of assembling. Exemplary pore-forming proteins that may be used in the compositions and methods of the present disclosure include α-hemolysin (e.g., from *S. aureus*), β-hemolysin, γ-hemolysin, aerolysin, cytolysin (e.g., pneumolysin), leukocidin, melittin, and porin A (e.g., MspA from *Mycobacterium smegmatis*)

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

"Nucleic acid," as used herein, generally refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Naturally occurring" or "wild-type" refers to the form found in nature. For example, a naturally occurring or wild-type protein is a protein having a sequence present in an organism that can be isolated from a source found in nature, and which has not been intentionally modified by human manipulation.

"Engineered," "recombinant," or "non-naturally occurring" when used with reference to, e.g., a cell, nucleic acid, or polypeptide, refers to a material that has been modified in a manner that would not otherwise exist in nature, or is identical thereto but produced or derived from synthetic materials and/or by manipulation using recombinant techniques.

"SpyCatcher protein," as used herein, refers to an amino acid sequence that comprises an N-terminal fragment of the CnaB2 domain of the *Streptococcus pycogenes* fibronectin binding protein, FbaB that includes Lys31 but excludes Asp117. CnaB2 N-terminal sequence fragments useful as SpyCatcher proteins in the methods of the present disclosure include the SpyCatcher proteins disclosed in Li et al., J.Mol.Biol. 2014 Jan. 23; 426(2): 309-317.

"SpyTag peptide," as used herein, refers to an amino acid sequence that comprises a C-terminal fragment of the CnaB2 domain of the *Streptococcus pycogenes* fibronectin binding protein, FbaB that includes Asp117 but excludes Lys31.

"Nanopore," as used herein, refers to a pore, channel, or passage formed or otherwise provided in a membrane or other barrier material that has a characteristic width or diameter of about 0.1 nm to about 1000 nm. A nanopore can be made of a naturally-occurring pore-forming protein, such as α-hemolysin from *S. aureus*, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Linker," as used herein, refers to any molecular moiety that provides a bonding attachment with some space between two or more molecules, molecular groups, and/or molecular moieties. Exemplary linkers that may be used in the compositions and methods of the present disclosure can include polymeric chains of two to 100 polyethylene glycol (PEG) moieties, which polymeric chains can further include alkyl, alkene, alkyne, ester, ether, amide, imide, and/or phosphodiester groups.

"Solid substrate," or "solid support," as used herein refers to any solid phase material to which a biomolecule can be attached. Exemplary solid-substrates that may be used with the compositions and methods of the present disclosure include beads, slides, wells, chips, made of various solid-phase materials including glass, polymer, and silicon.

Detailed Description Of Embodiments

The site-selective conjugation methods disclosed herein for the preparation of a conjugate between a protein, such as the pore-forming protein, α-hemolysin, and a biomolecule, such as DNA polymerase, generally require reagents comprising linkers and reactive groups (or reactive moieties) that react with groups on either the protein or the biomolecule. This conjugation method generally comprises the following steps (a), (b), and (c):

(a) contacting, under suitable reaction conditions, a protein, wherein the protein comprises a thiol group, with a compound of formula (I)

wherein, A is a thiol reactive group; $L_A$ is a linker; and X is a click chemistry reactive group; and thereby forming a modified protein of formula (II)

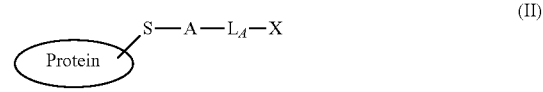

wherein S is a sulfur atom of a thiol group of the protein;
(b) contacting the modified protein of formula (II) with a compound of formula (III)

wherein, B is a reactive group; $L_B$ is a linker; and Y is a click chemistry reactive group that undergoes a click chemistry reaction with the cognate click chemistry reactive group X of compound of formula (II); thereby forming a modified protein of structural formula (IV)

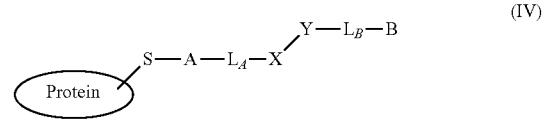

and,
(c) contacting the modified protein of formula (IV), under suitable reaction conditions, with a biomolecule capable of catalyzing the synthesis of a nucleotide polymer, wherein the biomolecule comprises a reactive group Z, wherein Z is capable of forming a covalent bond with the reactive group B, thereby forming the protein-biomolecule conjugate of formula (V).

As shown above, the general method requires reagent compounds of formula (I) and (III) and results in two modified protein intermediates of formulas (II) and (IV).

The protein-biomolecule conjugates of formula (V), thus results from three covalent bond forming reactions at each of steps (a), (b) and (c).

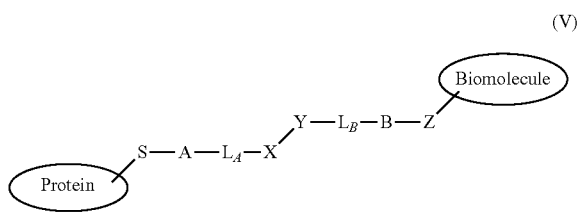

(V)

Step (a)

Step (a) comprises the covalent modification of a thiol group on the protein with a linker comprising a click chemistry reactive group of formula (I) resulting in a modified protein of formula (II). This step essentially modifies the protein such that it is capable of further modification via a facile and efficient click-chemistry reaction.

In some embodiments, the protein has one reactive thiol group such that the modified protein of formula (II) is modified at a single amino acid residue position. For example, the reactive thiol group can be the thiol group of a cysteine amino acid residue located on the surface of the protein or any other region exposed to solvent such that it can react with thiol reactive group A of the compound of formula (I). In some embodiments, the protein is a variant that has been engineered via recombinant DNA techniques so as to have only a single cysteine residue available for modification by the compound of formula (I).

In one embodiment, the protein is the pore-forming protein α-hemolysin from Staphyloccocus aureus (also referred to herein as "α-HL"). α-HL is one of the most-studied members of the class of pore-forming proteins, and has been sequenced, cloned, extensively characterized structurally and functionally using a wide range of techniques including site-directed mutagenesis and chemical labelling (see e.g., Valeva et al. (2001), and references cited therein). In particular, α-HL has had cysteine residue substitutions inserted at numerous positions allowing for covalent modification of the protein through maleimide linker chemistry (Ibid.) In some embodiments, the α-hemolysin useful in the methods of the present disclosure can be a non-naturally occurring engineered pore-forming protein α-hemolysin-C46 ("α-HL-C46"), which comprises α-hemolysin from S. aureus with a K46C amino acid residue substitution.

As shown by the structural depiction above, the compound of formula (I) generally comprises: a thiol reactive group, A, a linker, $L_A$, and a click chemistry reactive group, X. Generally, the compound of formula (I) should react efficiently and selectively under relatively mild aqueous conditions to form a covalent linkage between a thiol group on the protein and the click-chemistry reactive group, X. Further, the click chemistry reactive group, X, should not react with the protein under the conditions wherein the thiol reactive group A reacts with the thiol group of the protein, because X must be available to undergo a reaction with its cognate click chemistry reactive group, Y at step (b).

As noted above, the click chemistry reactive group, X must be selected so as to pair with its cognate click chemistry reactive group, Y used in step (b). Click chemistry reactive groups X and Y useful in the method can be selected from the following pairs of click chemistry reactive groups: azide and alkyne; azide and cyclooctyne; and azide and dibenzocyclooctyne-amine. Accordingly, in some embodiments of the compound of formula (I), the click chemistry reactive group, X is selected from alkyne, cyclooctyne, and dibenzocyclooctyne-amine. Alternatively, in some embodiments, the compound of formula (I), the click chemistry reactive group, X is an azide group.

Many thiol reactive groups that react selectively under mild conditions with protein cysteine groups are known in the art. Thiol reactive groups, A, known to be compatible with the above click-chemistry reactive group pairs and thus, particularly useful in the methods of the present disclosure as thiol reactive group A, are a maleimide group and a haloacetamide group. Accordingly, in some embodiments of the compound of formula (I), the thiol reactive group A is selected from a maleimide and a haloacetamide.

Generally, the linker, $L_A$ should provide a covalent tether while also providing adequate spacing between the protein and the click chemistry reactive group X, and ultimately the biomolecule that is conjugated via the method. Because the method of steps (a)-(c) comprises a second linker, $L_B$ in the compound of formula (III) used in step (b), the spacing provided by the combination of the two linkers, $L_A$ and $L_B$ that are part of the conjugate of formula (V), can also be considered.

Accordingly, in general embodiments of the present disclosure, the linker groups, $L_A$ and $L_B$ useful in the compounds of formula (I) and (III) for carrying out the site-selective conjugation method comprising steps (a)-(c) can include a covalently bonded chain of 2 to 100 atoms comprising one or more of the following chemical groups: linear ($C_1$-$C_5$) alkyl, linear ($C_1$-$C_5$) alkene, linear ($C_1$-$C_5$) alkyne, ester, ether, amine, amide, imide, phosphodiester, and/or polyethylene glycol (PEG). PEG linkers are well-known for use in conjugating biomolecules. Accordingly, in certain embodiments of the compositions of the present disclosure, the linkers $L_A$ and $L_B$ comprise a polymer of from 1 to 50 PEG moieties, in some embodiments, a polymer of from 2 to 25 PEG moieties, and in some embodiments, a polymer of from 2 to 15 PEG moieties. In some embodiments the linkers, $L_A$ and $L_B$ have different lengths and/or structures. It is also contemplated that in some embodiments $L_A$ and $L_B$ are the same.

Specific linker groups useful in the methods of the present disclosure are well-known and commercially available for use in conjugating or cross-linking proteins or other biomolecules. (See e.g., catalog of "crosslinking reagents" available from Thermo Scientific, USA at www.piercenet.com or Sigma-Aldrich, USA at www.sigmaaldrich.com).

Specific embodiments of the compounds of formula (I) are provided in greater detail below.

In some embodiments, the compound of formula (I) comprises a compound of formula (Ia) or (Ib) as shown in Table 1.

TABLE 1

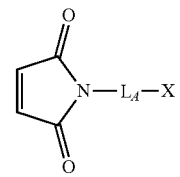

(Ia)

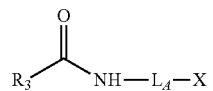

(Ib)

wherein $R_3$ is a halogen atom selected from F, Cl, Br, and I.

In some embodiments, the compound of formula (I) comprises a compound selected from compounds of formula (Ic), (Id), (Ie), (If), (Ig), and (Ih) as shown in Table 2.

TABLE 2

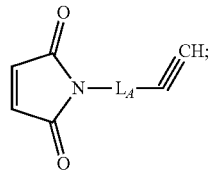
(Ic)

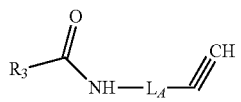
(Id)

wherein $R_3$ is a halogen atom selected from F, Cl, Br, and I;

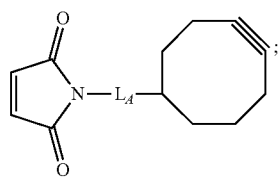
(Ie)

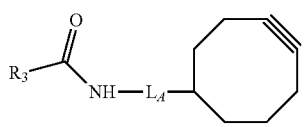
(If)

wherein $R_3$ is a halogen atom selected from F, Cl, Br, and I;

TABLE 2-continued (Ig)

(Ih)

wherein $R_3$ is a halogen atom selected from F, Cl, Br, and I.

In some embodiments, the compound of formula (I) comprises a compound selected from compounds of formula (Ii), and (Ij) as shown in Table 3.

TABLE 3

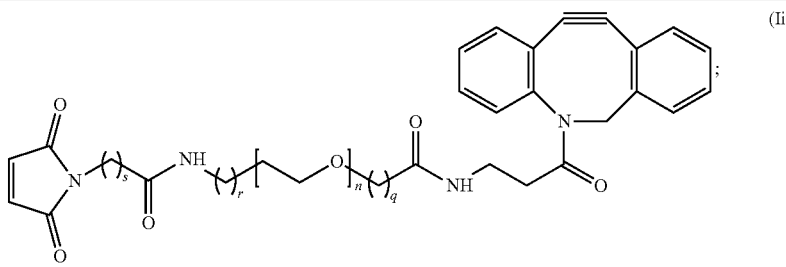
(Ii)

wherein,
n = 1 to 50, and q, r, and s each independently = 0, 1, 2, or 3

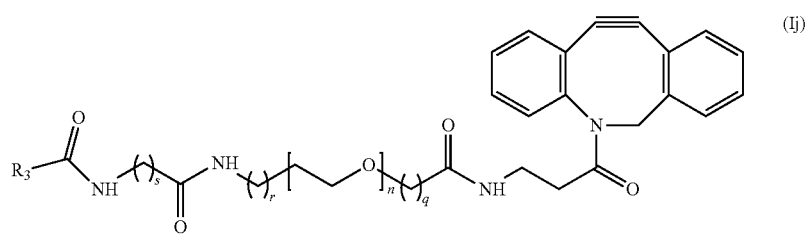
(Ij)

wherein,
n = 1 to 50, and q, r, and s each independently = 0, 1, 2, or 3; and
$R_3$ is a halogen atom selected from F, Cl, Br, and I.

In some embodiments, the compound of formula (I) comprises a compound selected from compounds of formula (Ik), and (Im) as shown in Table 4.

TABLE 4

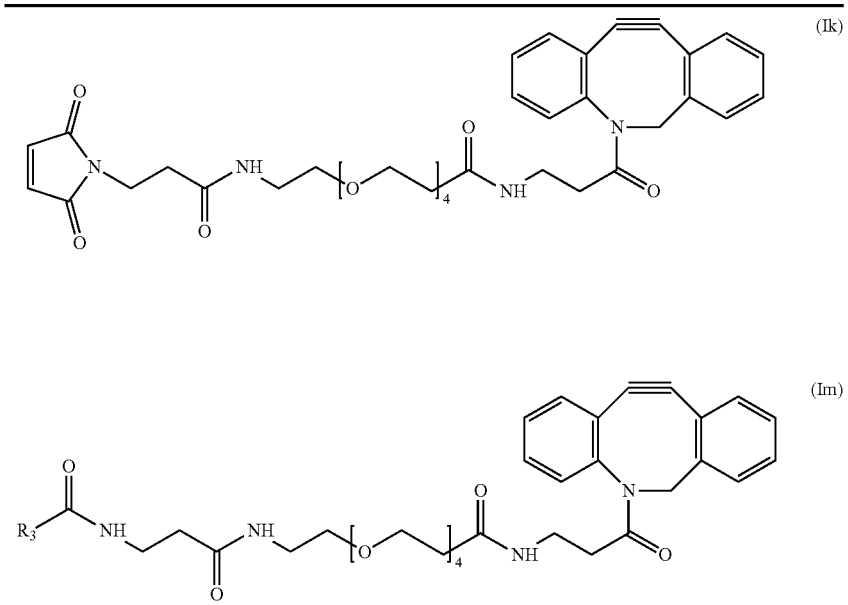

wherein $R_3$ is a halogen atom selected from F, Cl, Br, and I..

Step (b)

Step (b) comprises the click chemistry reaction the group X on the modified protein of formula (II), and the cognate click chemistry group Y on the reagent compound of formula (III). This step results in the intermediate modified protein compositions of formula (IV) and (IVa) (see above). It is the reactive group B on this intermediate compound of formula (IV) that undergoes the final site-selective reaction with the biomolecule in step (c).

As shown by the structural depiction above, the compound of formula (III) used as a reagent in step (b) generally comprises: a click chemistry reactive group, Y, a linker, $L_B$, and a reactive group, B. The click chemistry reactive group, Y must be selected so as to pair with its cognate click chemistry reactive group, X used in step (a). As noted above, click chemistry reactive groups X and Y useful in the method can be selected from the following pairs of click chemistry reactive groups: azide and alkyne; azide and cyclooctyne; and azide and dibenzocyclooctyne-amine. In some embodiments of the compound of formula (III), the click chemistry reactive group, Y is an azide group. An azide group will undergo a click chemistry reaction with cognate X groups selected from alkyne, cyclooctyne, and dibenzocyclooctyne-amine. Alternatively, in some embodiments, the compound of formula (III), the click chemistry reactive group, Y is selected from alkyne, cyclooctyne, and dibenzocyclooctyne-amine.

The cognate click chemistry reactive group Y of the reagent compound of formula (III) will react efficiently and selectively under relatively mild conditions to form a covalent linkage with the click-chemistry reactive group, X of the modified protein of formula (II). The resulting further modified protein of formula (IV) comprises a covalent linkage, depicted schematically herein (see compound of formula (IV) above) as a single line between X and Y, however, this linkage comprises heterocyclic (e.g., triazole) chemical moiety with a structure dependent on the two click chemistry reactive groups X and Y.

Generally, the linker, $L_B$ should provide a covalent tether while also providing adequate spacing between the protein and the click chemistry reactive group Y, and ultimately the biomolecule that is conjugated via the method. As noted above, because the method of steps (a)-(c) comprises two linkers, $L_A$ and $L_B$, the spacing provided by the combination of the two linkers in combination can be considered in selecting linker, $L_B$ in the compound of formula (III).

Accordingly, in some embodiments the linker group, $L_B$ useful in the compound of formula (III) can include a covalently bonded chain of 2 to 100 atoms comprising one or more of the following chemical groups: linear ($C_1$-$C_5$) alkyl, linear ($C_1$-$C_5$) alkene, linear ($C_1$-$C_5$) alkyne, ester, ether, amine, amide, imide, phosphodiester, and/or polyethylene glycol (PEG).

The selection of the linker $L_B$ can also depend on the reactive group B selected for the compound of formula (III). As discussed in greater detail below, a shorter linker $L_B$ (e.g., 2-3 carbons) can be used where the reactive group B is a SpyTag peptide, which comprises a chain of 13 amino acids, or a longer linker $L_B$ (e.g., 5-50 carbons) can be selected when the reactive group B is a benzyl thioester group.

Various embodiments of the modified protein of formula (IV), where the protein is a pore-forming protein as in (IVa), and that illustrate the various heterocyclic covalent linkage structures that can form upon click reaction of the reactive group Y and the reactive group X are shown below in Table 5 as compounds of formulas (IVb)-(IVi).

TABLE 5
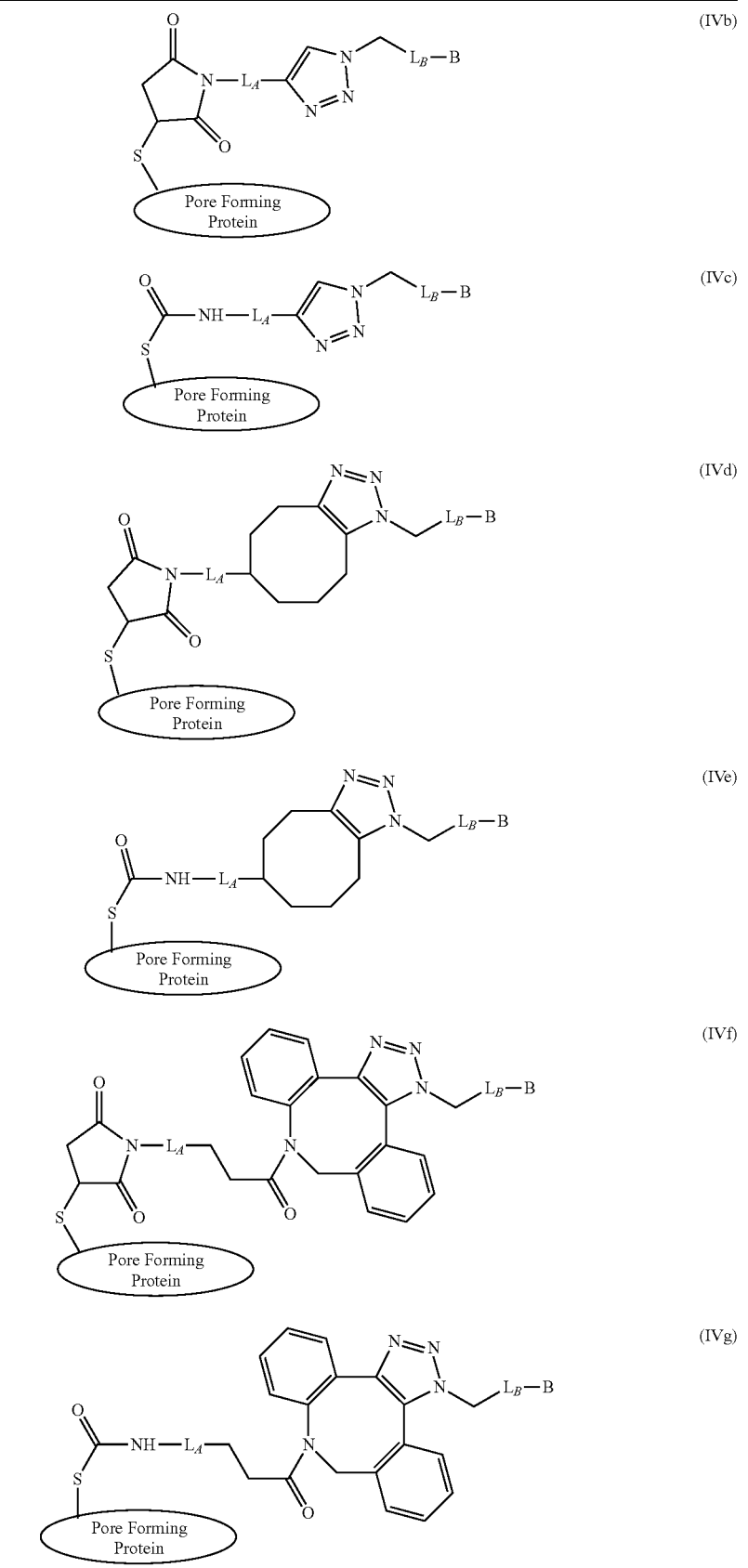

TABLE 5-continued

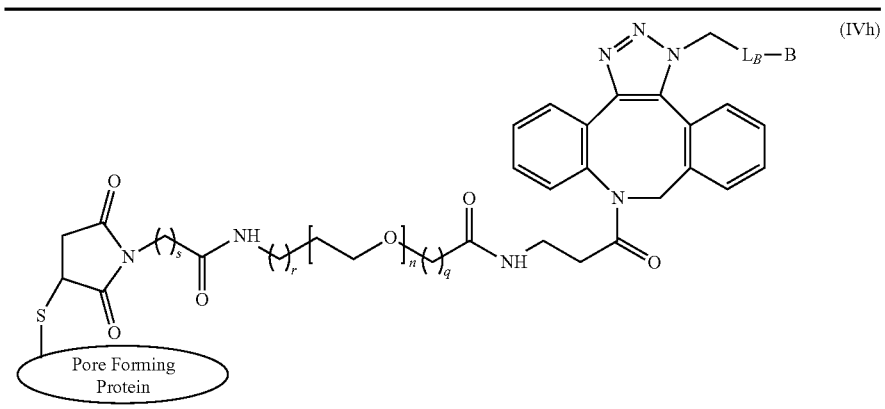
(IVh)

wherein, n = 1 to 50, and q, r, and s each independently = 0, 1, 2, or 3.

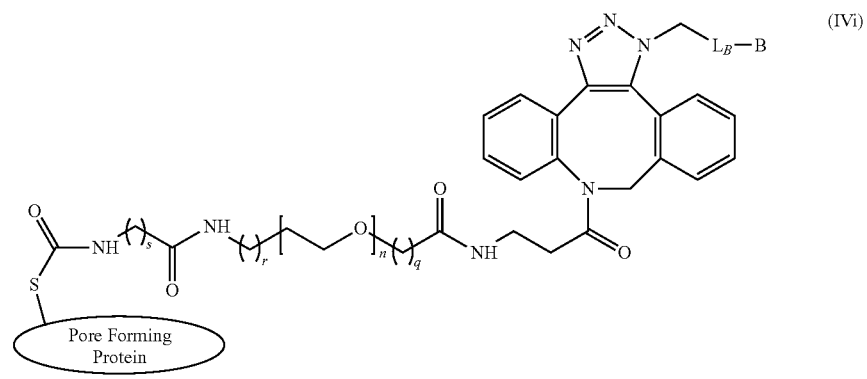
(IVi)

wherein, n = 1 to 50, and q, r, and s each independently = 0, 1, 2, or 3.

Generally, the selection of the reactive group B of the compound of formula (III) will depend on the reactive group Z which is the target group of the biomolecule for site-selective conjugation in the reaction of step (c).

In one embodiment, the reactive group Z of the biomolecule comprises an N-terminal cysteine residue and the reactive group B selected is a thioester. The thioester reactive group B can undergo a "Native Chemical Ligation" reaction (also referred to herein as "NCL reaction") that forms a covalent linkage comprising a peptide bond. (See e.g., Dawson et al., "Synthesis of proteins by native chemical ligation," Science 1994, 266, 776-779.) Embodiments of the compounds of formula (III) useful wherein the reactive group Z of the biomolecule comprises an N-terminal cysteine residue and a NCL reaction is used for conjugation are provided in greater detail below.

In some embodiments, where the reactive group Z comprises an N-terminal cysteine residue, the compound of formula (III) can comprise a compound of formula (IIIa) or (IIIb) as shown in Table 6.

TABLE 6

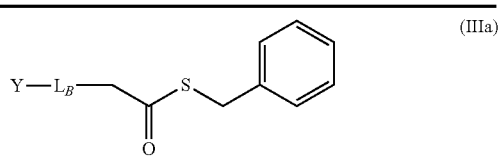
(IIIa)

TABLE 6-continued

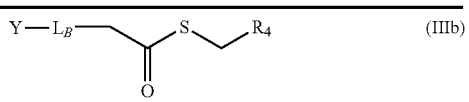
(IIIb)

wherein
$R_4$ is selected from the group consisting of linear or branched ($C_1$-$C_6$) alkyl, linear or branched ($C_1$-$C_6$) alkenyl, linear or branched ($C_1$-$C_6$) alkynyl, unsubstituted or para-substituted 6-membered aryl ring, and unsubstituted or para-substituted 6-membered heteroaryl ring.

In specific embodiments wherein the reactive group Z of the biomolecule comprises an N-terminal cysteine residue, the reactive group B is a benzyl thioester.

In further specific embodiments where the reactive group Z comprises an N-terminal cysteine residue, the compound of formula (III) can comprise a compound of formula (IIIc) or (IIId) as shown in Table 7.

TABLE 7

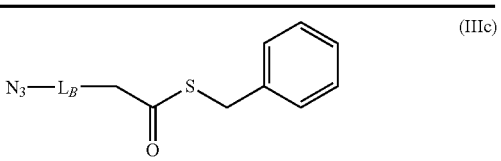
(IIIc)

TABLE 7-continued

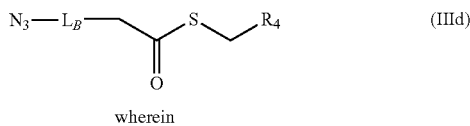

wherein
R$_4$ is selected from the group consisting of linear or branched (C$_1$-C$_6$) alkyl, linear or branched (C$_1$-C$_6$) alkenyl, linear or branched (C$_1$-C$_6$) alkynyl, unsubstituted or para-substituted 6-membered aryl ring, and unsubstituted or para-substituted 6-membered heteroaryl ring.

TABLE 8

Further, since the modified protein of formula (IV) is the result of step (b), it is contemplated that in some embodiments, the reactive group B of formula (IV) comprises a SpyTag peptide. Accordingly, in specific embodiments, the modified protein compound of formula (IV) can comprise a compound of formula (IVi) or (Vk) as shown in Table 9.

TABLE 9

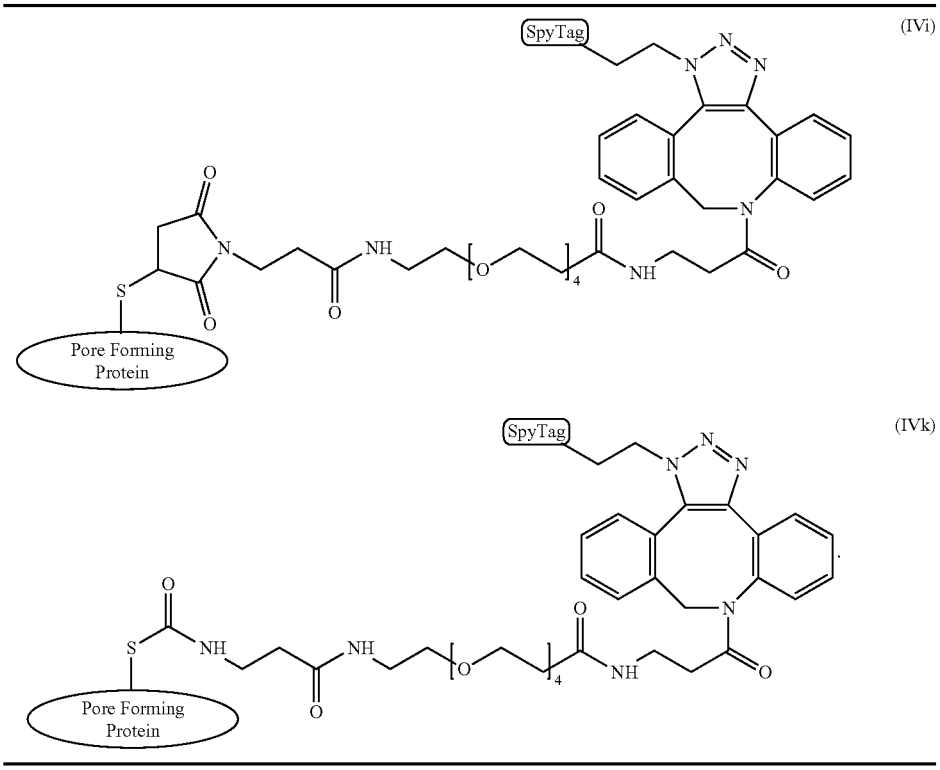

In another embodiment, the reactive group Z of the biomolecule comprises a SpyCatcher protein and the reactive group B selected is a SpyTag peptide. The SpyCatcher protein and SpyTag peptide undergo a reaction between a lysine residue of the protein and an aspartic acid residue of the peptide that results in a covalent linkage conjugating the two. (See e.g., Zakeri and Howarth (2010).JACS 132:4526-7; and Li et al., J.Mol.Biol. 2014 Jan. 23; 426(2): 309-317.) Embodiments of the compounds of formula (III) useful wherein the reactive group Z of the biomolecule comprises a SpyCatcher protein and the SpyCatcher-SpyTag reaction is used for conjugation are provided in greater detail below.

Generally, in the methods of the present disclosure when the reactive group Z comprises a SpyCatcher protein, the reactive group B of the compound of formula (III) should comprise a SpyTag peptide. Accordingly, in specific embodiments, the compound of formula (III) can comprise a compound of formula (IIIe) or (IIIf) as shown in Table 8.

As described elsewhere herein, the SpyTag peptide and SpyCatcher protein each comprise a fragment of an amino acid sequence of the CnaB2 domain from the *Streptococcus pyogenes* fibronectin binding protein FbaB. (See e.g., Li et al., J.Mol.Biol. 2014 Jan. 23; 426(2): 309-317). Generally, the SpyTag peptide comprises a reactive aspartic acid residue from a smaller C-terminal fragment (e.g., 8-20 amino acids), and the SpyCatcher protein comprises a reactive lysine residue from a larger N-terminal fragment (e.g., 100-140 amino acids). The reactive aspartic acid residue of the SpyTag peptide naturally binds to the SpyCatcher protein in an optimal conformation such that the aspartic acid reacts with the lysine to forms a covalent linkage between the two.

Exemplary C-terminal CnaB2 domain sequence fragments useful as SpyTag peptide in the methods and compositions of the present disclosure comprise the following 13 aa amino acid sequence from Li et al., J.Mol.Biol. 2014 Jan. 23; 426(2): 309-317: AHIVMVDAYKPTK (SEQ ID NO:

1). Other CnaB2 C-terminal sequence fragments useful as SpyTag peptides in the methods and compositions of the present disclosure can include shorter fragments of the SpyTag peptide of SEQ ID NO: 1, such as AHIVMVDAYK (SEQ ID NO: 2), and AHIVMVDA (SEQ ID NO: 3).

In some embodiments, it is contemplated that SpyTag peptides useful in the methods and compositions of the present disclosure can comprise additional amino acids, such as modified amino acids, which allow the SpyTag to be covalently attached to linkers. In some embodiments, the SpyTag can comprise an azido-modified amino acid at its N-terminus, such as 4-azido-L-homoalanine ("L-ahA"). Accordingly, an exemplary SpyTag peptide can comprise the following amino acid sequence: (L-ahA)AHIVMV-DAYKPTK (SEQ ID NO:4). A range of azido-, alkyne- and other group modified amino acids useful for click chemistry and other facile, high-efficiency covalent attachment chemistries are known in the art and commercially available.

The SpyCatcher protein can comprise a range of amino acid sequences that comprise an N-terminal fragment of the CnaB2 domain of the *Streptococcus pycogenes* fibronectin binding protein, FbaB that includes Lys31 but excludes Asp117.

In some embodiments, a SpyCatcher protein useful in the methods of the disclosure can include the 138 aa amino acid sequence of SEQ ID NO: 2.

A CnaB2 domain of the *Streptococcus pycogenes* fibronectin binding protein, FbaB, useful as a SpyCatcher protein in the methods of the present disclosure can include the following 144 aa sequence from Li et al., J.Mol.Biol. 2014 Jan. 23; 426(2): 309-317:

(SEQ ID NO: 5)
SYYHHHHHHDYDIPTTENLYFQGAMVDTLSGLSSEQGQSGDMTIEEDSAT

HIKFSKRDEDGKELAGATMELRDSSGKTISTWISDGQVKDFYLYPGKYTF

VETAAPDGYEVATAITFTVNEQGQVTVNGKATKGDAHIVMVDA.

An exemplary N-terminal CnaB2 domain sequence fragment useful as SpyCatcher protein in the methods of the present disclosure includes the following 129 aa amino acid sequence:

(SEQ ID NO: 6)
DYDIPTTENLYFQGAMVDTLSGLSSEQGQSGDMTIEEDSATHIKFSKRDE

DGKELAGATMELRDSSGKTISTWISDGQVKDFYLYPGKYTFVETAAPDGY

EVATAITFTVNEQGQVTNNGKATKGDAHI.

In some embodiments, the N-terminal CnaB2 domain sequence fragment useful as SpyCatcher protein in the methods of the present disclosure includes the following 138 aa amino acid sequence from Li et al., J.Mol.Biol. 2014 Jan. 23; 426(2): 309-317:

(SEQ ID NO: 7)
SYYHHHHHHDYDIPTTENLYFQGAMVDTLSGLSSEQGQSGDMTIEEDSAT

HIKFSKRDEDGKELAGATMELRDSSGKTISTWISDGQVKDFYLYPGKYTF

VETAAPDGYEVATAITFTVNEQGQVTVNGKATKGDAHI.

It is contemplated that SpyCatcher proteins useful in the methods and conjugate compositions of the present disclosure can comprise additional amino acid linkers at the N- and C-terminii to facilitate purification and fusion to a biomolecule (e.g., DNA polymerase). An exemplary Spy-Catcher protein comprising additional amino acid sequences (e.g., N-terminal His tag and C-terminal GGS linker) has the following 143 aa sequence:

(SEQ ID NO: 8)
MHHHHHHHSGDYDIPTTENLYFQGAMVDTLSGLSSEQGQSGDMTIEEDS

ATHIKFSKRDEDGKELAGATMELRDSSGKTISTWISDGQVKDFYLYPGKY

TFVETAAPDGYEVATAITFTVNEQGQVTVNGKATKGDAHIGGS.

In some embodiments of methods and compositions of the present disclosure, it is contemplated that a fusion of a SpyCatcher protein and a biomolecule can be used. In some embodiments, the fusion comprises a SpyCatcher protein sequence attached via its C-terminus to the N-terminus of the biomolecule aa sequence, wherein the fusion optionally comprises a polypeptide linker sequence between the Spy-Catcher protein and the biomolecule.

Similarly, the SpyTag peptide can comprise a range of amino acid sequences that comprise a C-terminal fragment of the CnaB2 domain of the *Streptococcus pycogenes* fibronectin binding protein, FbaB that includes Asp117 but excludes Lys31. In some embodiments, a SpyTag peptide useful in the methods and compositions of the present disclosure can include an amino acid sequence selected from SEQ ID NO: 1, 2, 3, and 4. In one embodiment, the SpyTag peptide comprises the amino acid sequence of SEQ ID NO: 1.

Step (c)

Step (c) comprises the final covalent linkage forming reaction between reactive group B of the modified protein of structural formula (IV) and reactive group Z of the biomolecule. This reaction results in the formation of the protein-biomolecule conjugate composition of formula (V). As described above, the selection of the reactive groups B and Z will dictate suitable reaction conditions for step (c). Both the NCL reaction conditions and the SpyTag-SpyCatcher reaction conditions are well-known in the art and useful in the step (c) reaction of the present disclosure. (See e.g., Dawson et al., (1994) Science 266, 776-779; Zakeri and Howarth (2010) JACS 132:4526-7; and Li et al. (2014) J.Mol.Biol. 23; 426(2): 309-317.)

Various embodiments of the protein-biomolecule conjugate composition of formula (V) that is the product of step (c) reaction are shown below in Table 10 as compounds of formulas (Vb)-(Vm).

TABLE 10
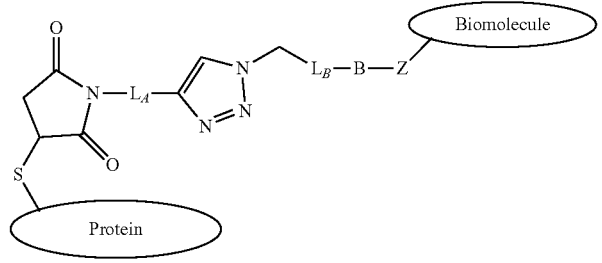 (Vb)
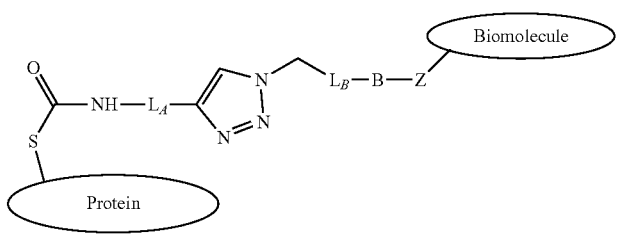 (Vc)
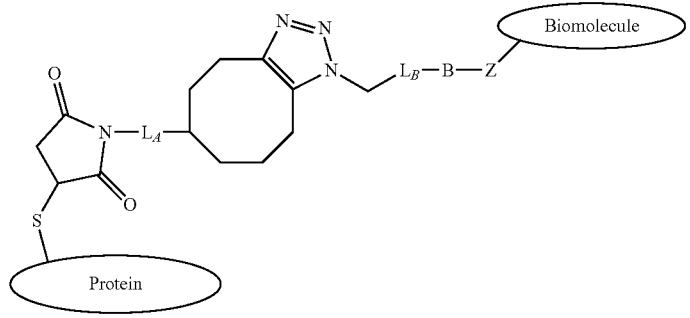 (Vd)
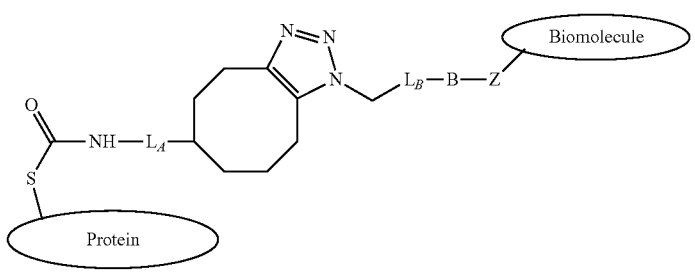 (Ve)
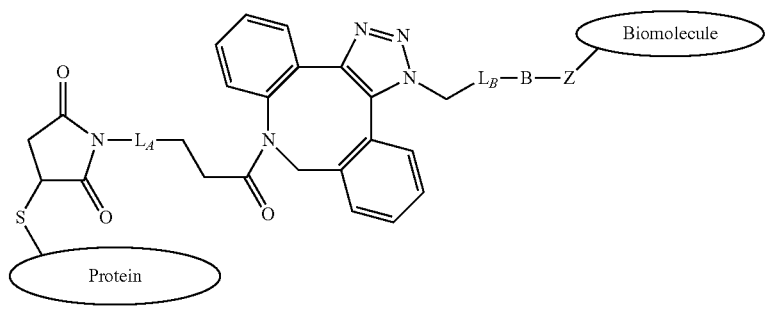 (Vf)

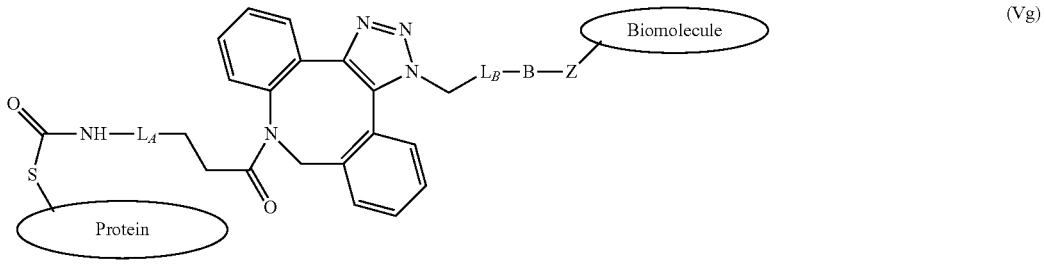
(Vg)
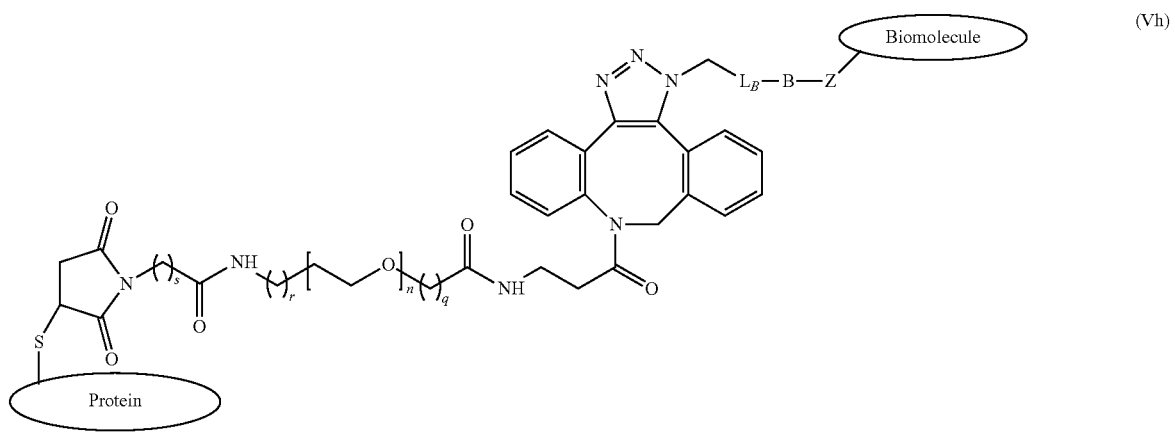
(Vh)
wherein, n = 1 to 50, and q, r, and s each independently = 0, 1, 2, or 3.
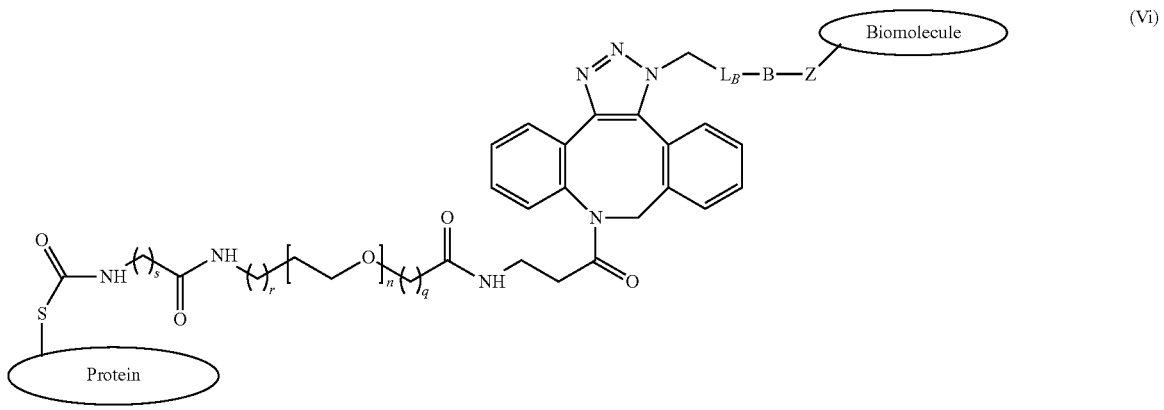
(Vi)
wherein, n = 1 to 50, and q, r, and s each independently = 0, 1, 2, or 3.
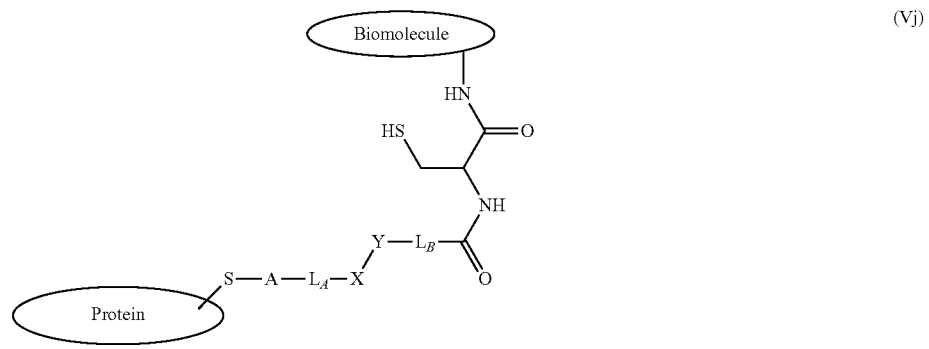
(Vj)

TABLE 10-continued

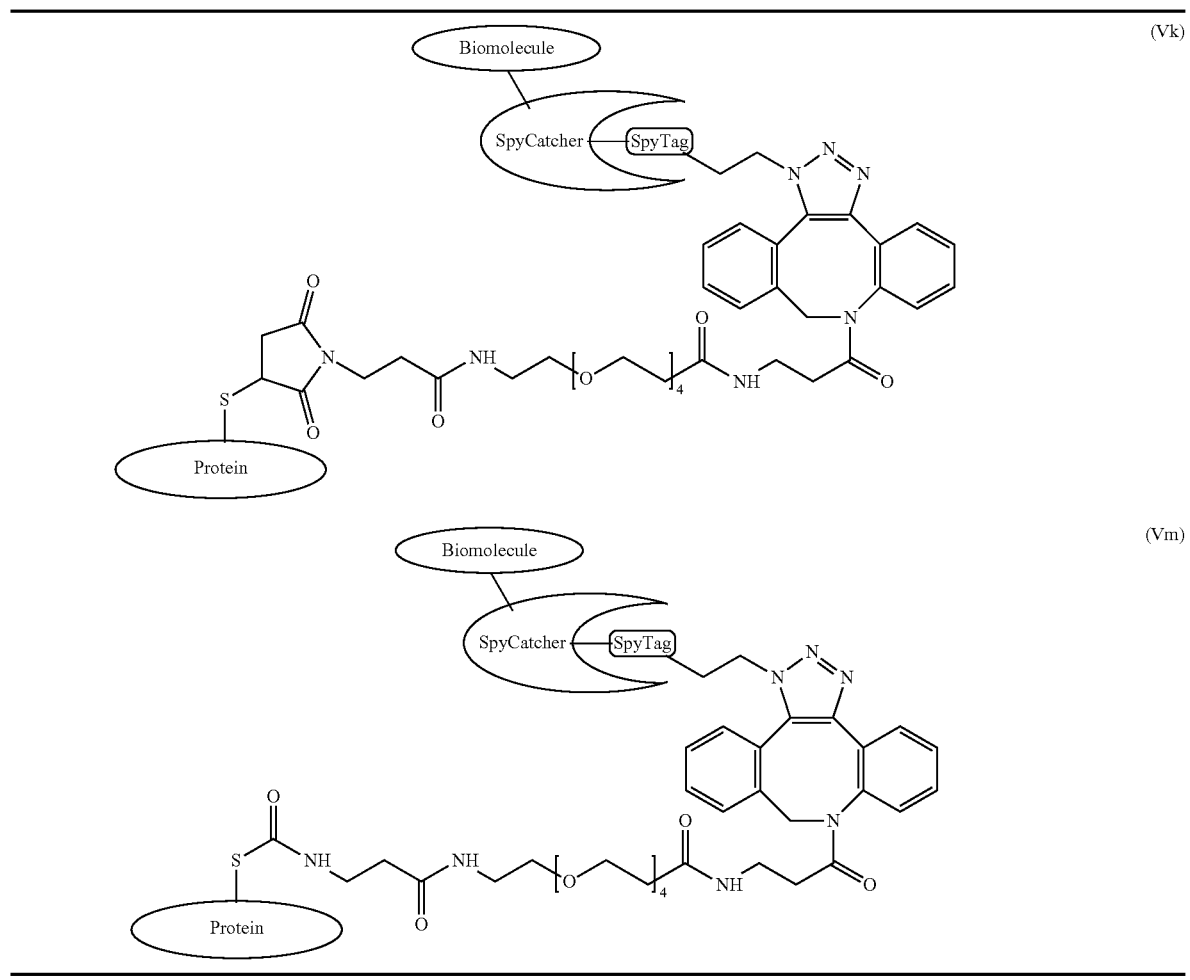

The disclosed site-selective conjugation methods comprising steps (a)-(c) allow for fast, efficient conjugation between proteins and other biomolecules at relatively low concentrations and without large mole excesses of one reagent over the other. Accordingly, the compositions and chemical processes for preparing the conjugates disclosed herein are particularly well-suited for use in preparing nanopore compositions comprising a pore-forming protein embedded in a membrane covalently linked to a biomolecule, such as a DNA polymerase. Such nanopore compositions can be used in applications requiring nanopore detection, including single-molecule DNA sequencing-by-synthesis.

The general site-selective conjugation methods comprising steps (a)-(c) disclosed herein can be used with a wide range of pore-forming proteins, in both naturally-occurring, and non-naturally occurring (e.g., engineered or recombinant) forms of the protein. A wide range of pore-forming proteins are known in the art, and the conjugation reagents and methods provided herein should be broadly applicable to them due to their common amino acid polymeric structure. Accordingly, in some embodiments of the present disclosure, the pore-forming protein used in the methods comprising steps (a)-(c) are selected from the group consisting of α-hemolysin, β-hemolysin, γ-hemolysin, aerolysin, cytolysin, leukocidin, melittin, MspA porin and porin A.

It is a surprising advantage of the site-selective conjugation methods comprising steps (a)-(c) disclosed herein that the conjugate compositions of formula (V) are formed fast and efficiently even though both the pore-forming protein and the biomolecule are large proteins, and accordingly only available in the reaction solution in relatively low concentrations. For example, in some embodiments of the methods of preparation of the conjugate compositions of formula (I), the protein and/or the biomolecule are present in the reaction solution at a concentration of less than 1000 µM, 750 µM, 500 µM, 250 µM, 100 µM, 50 µM, 10 µM, 5 µM, or 1 µM or less.

Because the quick and efficient site-selective conjugation methods comprising steps (a)-(c) allow for such low reactant concentrations, the compositions and methods of preparation proteins and biomolecules in much higher weight ranges. Thus, in some embodiments of the compositions and methods of preparation disclosed herein, the protein has a molecular weight of at least 20 kDa, 30 kDa, 40 kDa, 50 kDa, or greater. In some embodiment of the composition, the biomolecule has a molecular weight of at least 30 kDa, 40 kDa, 50 kDa, 60 kDa, 70 kDa, 80 kDa, or greater. In some embodiments, the protein has a molecular weight of at least 30 kDa and the biomolecule has a molecular weight of at least 50 kDa.

Moreover, the site-selective conjugation method comprising steps (a)-(c) has the surprising advantage of allowing for the formation of conjugates of formula (II), (IV), and (V) wherein the protein is part of a large multimeric protein complex. Accordingly, in some embodiments of the compositions and methods of preparation disclosed herein, the protein is pore-forming protein that is a part of a multimeric complex, wherein the multimer is selected from hexamer, heptamer, octamer, nonamer, decamer, or larger multimer. In some embodiments, the pore-forming protein is a single monomer which is part of a multmeric complex, wherein the other monomers of the complex are not modified in the method of steps (a)-(c) (i.e., only a single monomer of the multimer is conjugated to the biomolecule).

Generally, the pore-forming proteins useful in the embodiments of the present disclosure are capable of spontaneously self-assembling nanopores in membranes, wherein the nanopore has a diameter in a range from about 0.5 nanometer to about 25 nanometers. In some embodiments of the compositions and methods disclosed herein, the protein is a pore-forming protein that is embedded in a membrane, and thereby forming a nanopore through the membrane (or other barrier material). Accordingly, in some embodiments, the protein is pore-forming protein that is part of a nanopore, and/or is part of a multimeric protein complex or assembly that forms a nanopore.

Where the pore-forming protein is α-HL, a heptameric complex of the α-HL monomers can spontaneously form a nanopore in a lipid bilayer. It has been shown that heptamers of α-HL comprising a ratio of 6:1 native α-HL to mutant α-HL can form nanopores (see e.g., Valeva et al. (2001), and references cited therein). Accordingly, in some embodiments, the compositions and methods of the present disclosure can comprise a nanopore, wherein the nanopore comprises a heptameric α-HL complex, which has 6:1 native α-HL to α-HL-C46, and further wherein the α-HL-C46 is conjugated to a biomolecule in carrying out steps (a)-(c). In some embodiments, the biomolecule conjugated to the nanopore is a DNA polymerase.

Further it is contemplated that the site-selective conjugation method comprising steps (a)-(c) can be carried out wherein the protein is a pore-forming protein that is part of a multimeric complex that has formed a nanopore. Thus, in some embodiments, the method of forming the conjugate comprises first forming a nanopore comprising a pore-forming protein then carrying out steps (a)-(c) of the method wherein the pore-forming protein is part of a multimer. Accordingly, in some embodiments, the present disclosure provides a composition comprising a heptameric α-HL nanopore, wherein at least one of the α-HL monomer units is covalently modified as in compounds of formula (II), (IV), and (V). In some embodiments, the heptameric α-HL nanopore comprises 6 native α-HL monomers and 1 α-HL mutant monomer that comprises an amino acid residue covalently modified with a click reactive group X, as in the compound of formula (II). In some embodiments, the 1 α-HL mutant monomer is α-HL-C46, which comprises a single cysteine residue.

In some embodiments, it is contemplated that the site-selective conjugation method comprising steps (a)-(c) can be carried out wherein the protein is a pore-forming protein that is part of a nanopore that is in solution. However, it is also contemplated that in some embodiments of the conjugation method of steps (a)-(c) can be carried out wherein the pore-forming protein is part of a nanopore that is immobilized, such as through covalent or non-covalent attachment (directly or indirectly) to a solid support.

It is contemplated that nanopores comprising a pore-forming protein conjugate composition of formula (V) of the present disclosure can be used in typical nanopore applications and devices, such as single-molecule nucleic acid sequencing. Nanopore devices and methods for making and using them are disclosed in e.g., U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2013/0264207, 2013/0244340, 2004/0121525, and 2003/0104428, each of which are hereby incorporated by reference in their entirety. In such nanopore embodiments, the pore-forming protein typically is embedded in a membrane attached to a solid substrate. Typically, the solid substrate comprises a material selected from the group consisting of polymer, glass, silicon, and a combination thereof. Additionally, the solid substrate can further comprise adjacent to the nanopore, a sensor, a sensing circuit, or an electrode coupled to a sensing circuit, optionally, a complementary metal-oxide semiconductor (CMOS), or field effect transistor (FET) circuit.

Generally, biomolecules useful in the embodiments of the present disclosure can be any protein or nucleic acid that might be desirable to conjugate with a pore-forming protein, and thereby position adjacent to a nanopore, and accompanying nanopore detection system. In one embodiment it is contemplated that the conjugate compositions of the present disclosure can be used in nanopore-based nucleic acid sequencing devices. Accordingly, in some embodiments of the compositions and methods disclosed herein, the biomolecule is an enzyme capable of catalyzing the synthesis of a nucleotide polymer. In some embodiments, the biomolecule is an enzyme selected from the group consisting of a DNA polymerase, RNA polymerase, reverse transcriptase, and DNA ligase. In some embodiments, the biomolecule is a naturally-occurring or non-naturally occurring (e.g., engineered) enzyme that has 5'→3' DNA polymerase activity and strong strand displacement activity but lacks 5'→3' exonuclease activity.

A wide range of polymerases and ligases are known in the art, and the conjugation reagents and methods provided herein should be broadly applicable to them due to their common amino acid polymeric structure. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1). In some embodiments, the biomolecule comprises a DNA polymerase from *Bacillus stearothermophilus*. In some embodiments, the biomolecule comprises the large fragment of DNA polymerase from *B. stearothermophilus*. In one embodiment, the biomolecule is DNA polymerase Bst 2.0 (commercially available from New England Bio-Labs, Inc., Massachusetts, USA). In some embodiments, the biomolecule is 9° N polymerase, *E. Coli* DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase).

In some embodiments, a DNA polymerase useful in the methods and conjugate compositions of the present disclosure is Pol6, which has the following 726 aa sequence:

(SEQ ID NO: 9)
DKHTQYVKEHSFNYDEYKKANFDKIECLIFDTESCTNYENDNTGARVYGW

GLGVTRNHNMIYGQNLNQFWEVCQNIFNDWYHDNKHTIKITKTKKGFPKR

KYIKFPIAVHNLGWDVEFLKYSLVENGFNYDKGLLKTVFSKGAPYQTVTD

-continued

VEEPKTFHIVQNNNIVYGCNVYMDKFFEVENKDGSTTEIGLCLDFFDSYK

IITCAESQFHNYVHDVDPMFYKMGEEYDYDTWRSPTHKQTTLELRYQYND

IYMLREVIEQFYIDGLCGGELPLTGMRTASSIAFNVLKKMTFGEEKTEEG

YINYFELDKKTKFEFLRKRIEMESYTGGYTHANHKAVGKTINKIGCSLDI

NSSYPSQMAYKVFPYGKPVRKTWGRKPKTEKNEVYLIEVGFDFVEPKHEE

YALDIFKIGAVNSKALSPITGAVSGQEYFCTNIKDGKAIPVYKELKDTKL

TTNYNVVLTSVEYEFWIKHFNFGVFKKDEYDCFEVDNLEFTGLKIGSILY

YKAEKGKFKPYVDHFTKMKVENKKLGNKPLTNQAKLILNGAYGKFGTKQN

KEEKDLIMDKNGLLTFTGSVTEYEGKEFYRPYASFVTAYGRLQLWNAIIY

AVGVENFLYCDTDSIYCNREVNSLIEDMNAIGETIDKTILGKWDVEHVFD

KFKVLGQKKYMYHDCKEDKTDLKCCGLPSDARKIIIGQGFDEFYLGKNVE

GKKQRKKVIGGCLLLDTLFTIKKIMF.

As described elsewhere herein, a fusion polypeptide of the biomolecule (e.g., DNA polymerase) and a SpyCatcher protein can be used in the methods and compositions of the present disclosure. Accordingly, in some embodiments, a fusion of the SpyCatcher protein sequence with His tag and linker of SEQ ID NO: 8 and the 726 amino acid Pol6 polymerase sequence of SEQ ID NO: 9. One such exemplary fusion polypeptide of DNA polymerase Pol6 and a SpyCatcher protein useful in the methods and compositions of the present disclosure comprises the following 875 amino acid sequence:

(SEQ ID NO: 10)
MHHHHHHHHSGDYDIPTTENLYFQGAMVDTLSGLSSEQGQSGDMTIEEDS

ATHIKFSKRDEDGKELAGATMELRDSSGKTISTWISDGQVKDFYLYPGKY

TFVETAAPDGYEVATAITFTVNEQGQVTVNGKATKGDAHIGGSDKHTQYV

KEHSFNYDEYKKANFDKIECLIFDTESCTNYENDNTGARVYGWGLGVTRN

HNMIYGQNLNQFWEVCQNIFNDWYHDNKHTIKITKTKKGFPKRKYIKFPI

AVHNLGWDVEFLKYSLVENGFNYDKGLLKTVFSKGAPYQTVTDVEEPKTF

HIVQNNNIVYGCNVYMDKFFEVENKDGSTTEIGLCLDFFDSYKIITCAES

QFHNYVHDVDPMFYKMGEEYDYDTWRSPTHKQTTLELRYQYNDIYMLREV

IEQFYIDGLCGGELPLTGMRTASSIAFNVLKKMTFGEEKTEEGYINYFEL

DKKTKFEFLRKRIEMESYTGGYTHANHKAVGKTINKIGCSLDINSSYPSQ

MAYKVFPYGKPVRKTWGRKPKTEKNEVYLIEVGFDFVEPKHEEYALDIFK

IGAVNSKALSPITGAVSGQEYFCTNIKDGKAIPVYKELKDTKLTTNYNVV

LTSVEYEFWIKHFNFGVFKKDEYDCFEVDNLEFTGLKIGSILYYKAEKGK

FKPYVDHFTKMKVENKKLGNKPLTNQAKLILNGAYGKFGTKQNKEEKDLI

MDKNGLLTFTGSVTEYEGKEFYRPYASFVTAYGRLQLWNAIIYAVGVENF

LYCDTDSIYCNREVNSLIEDMNAIGETIDKTILGKWDVEHVFDKFKVLGQ

KKYMYHDCKEDKTDLKCCGLPSDARKIIIGQGFDEFYLGKNVEGKKQRKK

VIGGCLLLDTLFTIKKIMF.

The ordinary artisan would recognize that the exemplary 875 aa SpyCatcher-Pol6 fusion polypeptide sequence of SEQ ID NO: 10 can be encoded by any of a broad range of degenerate nucleotide (nt) coding sequences. In one embodiment, the SpyCatcher-Pol6 fusion sequence is encoded by the 2610 nt sequence:

(SEQ ID NO: 11)
ATGCATCACCATCATCATCACCACCACAGCGGTGACTACGACATCCCGAC

CACCGAGAACCTGTACTTCCAGGGCGCCATGGTGGACACACTGAGCGGTC

TGAGCAGTGAACAGGGCCAGAGCGGCGACATGACCATTGAAGAGGACAGC

GCCACCCACATCAAGTTCAGCAAGCGTGACGAGGACGGTAAGGAACTGGC

CGGCGCCACCATGGAACTGCGTGACAGCAGCGGCAAGACCATCAGCACCT

GGATCAGCGATGGCCAGGTGAAGGACTTCTACCTGTACCCGGGCAAGTAC

ACCTTCGTGGAGACAGCCGCACCGGACGGTTACGAGGTTGCCACCGCCAT

CACCTTCACCGTGAACGAGCAGGGCCAAGTGACCGTTAACGGCAAGGCCA

CCAAGGGTGACGCCCACATCGGCGGTTCCGACAAACACACGCAGTACGTC

AAAGAGCATAGCTTCAATTATGACGAGTATAAGAAAGCGAATTTCGACAA

GATCGAGTGCCTGATCTTTGACACCGAGAGCTGCACGAATTATGAGAACG

ATAATACCGGTGCACGTGTTTACGGTTGGGGTCTTGGCGTCACCCGCAAC

CACAATATGATCTACGGCCAAAATCTGAATCAGTTTTGGGAAGTATGCCA

GAACATTTTCAATGATTGGTATCACGACAACAAACATACCATTAAGATTA

CCAAGACCAAGAAAGGCTTCCCGAAACGTAAGTACATTAAGTTTCCGATT

GCAGTTCACAATTTGGGCTGGGATGTTGAATTCCTGAAGTATAGCCTGGT

GGAGAATGGTTTCAATTACGACAAGGGTCTGCTGAAAACTGTTTTTAGCA

AGGGTGCGCCGTACCAAACCGTGACCGATGTTGAGGAACCGAAAACGTTC

CATATCGTCCAGAATAACAACATCGTTTATGGTTGTAACGTGTATATGGA

CAAATTCTTTGAGGTCGAGAACAAAGACGGCTCTACCACCGAGATTGGCC

TGTGCTTGGATTTCTTCGATAGCTATAAGATCATCACGTGTGCTGAGAGC

CAGTTCCACAATTACGTTCATGATGTGGATCCAATGTTCTACAAAATGGG

TGAAGAGTATGATTACGATACTTGGCGTAGCCCGACGCACAAGCAGACCA

CCCTGGAGCTGCGCTACCAATACAATGATATCTATATGCTGCGTGAAGTC

ATCGAACAGTTTTACATTGACGGTTTATGTGGCGGCGAGCTGCCGCTGAC

CGGCATGCGCACCGCTTCCAGCATTGCGTTCAACGTGCTGAAAAAGATGA

CCTTTGGTGAGGAAAAGACGGAAGAGGGCTACATCAACTATTTTGAATTG

GACAAGAAAACCAAATTCGAGTTTCTGCGTAAGCGCATTGAAATGGAATC

GTACACCGGTGGCTATACGCACGCAAATCACAAAGCCGTTGGTAAGACTA

TTAACAAGATCGGTTGCTCTTTGGACATTAACAGCTCATACCCTTCGCAG

ATGGCGTACAAGGTCTTTCCGTATGGCAAACCGGTTCGTAAGACCTGGGG

TCGTAAACCAAAGACCGAGAAGAACGAAGTTTATCTGATTGAAGTTGGCT

TTGACTTCGTGGAGCCGAAACACGAAGAATACGCGCTGGATATCTTTAAG

ATTGGTGCGGTGAACTCTAAAGCGCTGAGCCCGATCACCGGCGCTGTCAG

CGGTCAAGAGTATTTCTGTACGAACATTAAAGACGGCAAAGCAATCCCGG

TTTACAAAGAACTGAAGGACACCAAATTGACCACTAACTACAATGTCGTG

CTGACCAGCGTGGAGTACGAGTTCTGGATCAAACACTTCAATTTTGGTGT

GTTTAAGAAAGACGAGTACGACTGTTTCGAAGTTGACAATCTGGAGTTTA

-continued

```
CGGGTCTGAAGATTGGTTCCATTCTGTACTACAAGGCAGAGAAAGGCAAG

TTTAAACCTTACGTGGATCACTTCACGAAAATGAAAGTGGAGAACAAGAA

ACTGGGTAATAAGCCGCTGACGAATCAGGCAAAGCTGATTCTGAACGGTG

CGTACGGCAAATTCGGCACCAAACAAAACAAAGAAGAGAAAGATTTGATC

ATGGATAAGAACGGTTTGCTGACCTTCACGGGTAGCGTCACGGAATACGA

GGGTAAAGAATTCTATCGTCCGTATGCGAGCTTCGTTACTGCCTATGGTC

GCCTGCAACTGTGGAACGCGATTATCTACGCGGTTGGTGTGGAGAATTTT

CTGTACTGCGACACCGACAGCATCTATTGTAACCGTGAAGTTAACAGCCT

CATTGAGGATATGAACGCCATTGGTGAAACCATCGATAAAACGATTCTGG

GTAAATGGGACGTGGAGCATGTCTTTGATAAGTTTAAGGTCCTGGGCCAG

AAGAAGTACATGTATCATGATTGCAAAGAAGATAAAACGGACCTGAAGTG

TTGCGGTCTGCCGAGCGATGCCCGTAAGATTATCATTGGTCAAGGTTTCG

ACGAGTTTTATCTGGGCAAAAATGTCGAAGGTAAGAAGCAACGCAAAAAA

GTGATCGGCGGTTGCCTGCTGCTGGACACCCTGTTTACGATCAAGAAAAT

CATGTTCTAA.
```

In specific embodiments, the present disclosure provides methods of steps (a)-(c) and associated compositions comprising compounds of formula (I), (II), (III), (IV), and (V), wherein the linkers $L_A$ and $L_B$ are independently selected from the group consisting of structures of formula (VIa)-formula (VIe) shown below in Table 11.

TABLE 11

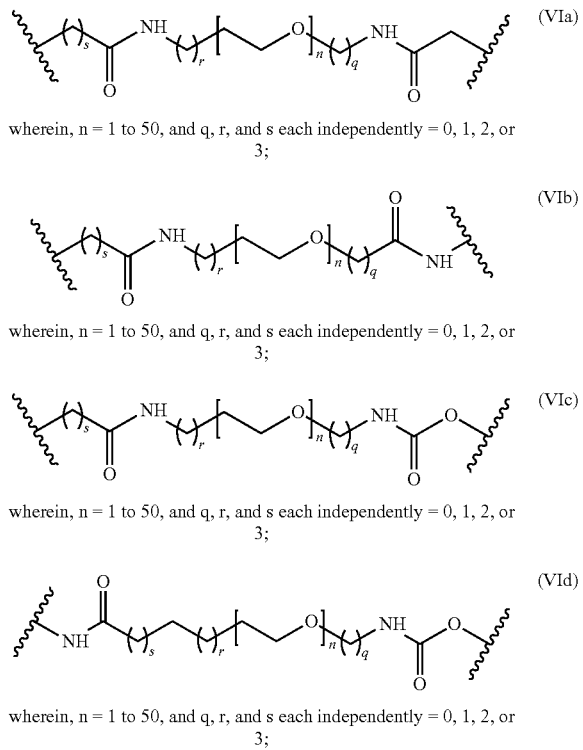

wherein, n = 1 to 50, and q, r, and s each independently = 0, 1, 2, or 3;

TABLE 11-continued

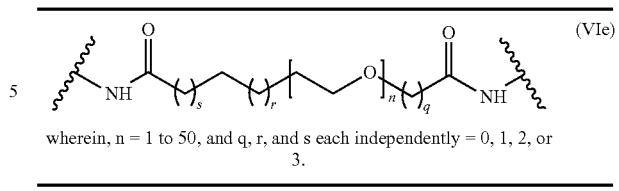

wherein, n = 1 to 50, and q, r, and s each independently = 0, 1, 2, or 3.

EXAMPLES

Example 1

Site-Selective Conjugation of a Pore-Forming Protein to a Polymerase using Click-Chemistry and Native Chemical Ligation This example illustrates the use of the site-selective conjugation method of steps (a)-(c) disclosed herein, wherein the B and Z reactive groups undergo a native chemical ligation (NCL) reaction in step (c). The example demonstrates preparation of a composition of formula (V), wherein the cysteine side-chain of an α-HL-C46 pore-forming protein that is part of a heptameric nanopore complex is conjugated to the N-terminus of a DNA polymerase (Pol), as depicted schematically in FIG. 1.

Materials and Methods

A. Pore-forming protein (e.g., α-HL) purification: The pore-forming protein monomers used are native α-HL and an engineered α-HL-C46, both encoded with 6-His tags for purification. The K46C (lysine at position 46 substituted with cysteine) mutant of a S. aureus α-HL monomer with a 6-His tag ("α-HL-C46") is prepared using standard protein engineering techniques (see e.g., Valeva et al. (2001) and Palmer et al. (1993)). The native α-HL and the α-HL-C46 monomers are recombinantly expressed in E. coli, and affinity purified using standard techniques. Briefly, the wild-type α-HL and α-HL-C46 are purified as described in the protocol for "PrepEase" His-tagged protein purification kits (USB-Affymetrix; USA) and exchanged into 1×PBS with 1 mM tris-carboxyethyl-phosphine (TCEP) at pH 7.2 at 1.0 mg/mL protein concentration. All α-HL purification steps are performed in the presence of reducing agent (TCEP or DTT).

B. 6:1 heptameric nanopore formation: Purified α-HL-C46 is mixed with wild-type α-HL in the presence of lipid to form heptamers as follows. To obtain a heptameric pore complex with the optimal 6:1 ratio of native α-HL monomers to the α-HL-C46 mutant monomer, an 11:1 ratio is used for oligomerization. Lipid (1,2-diphytanoyl-sn-glycero-3-phosphocholine, powder, Avanti Polar Lipids) is added to a final concentration of 5 mg/mL in 50 mM tris, 200 mM NaCl, pH 8.0 for 30 minutes at 40° C. 5% octyl-beta-glucoside (β-OG) is added to pop vesicles, as assessed by clearing, to solubilize the proteins. Then samples are concentrated using 100K MWCO filters and spun at 24000 RPM for 30 minutes to pellet the precipitated protein. After equilibrating size-exclusion columns with 30 mM βOG, 75 mM KCl, 20 mM HEPES at pH 7.5, 500 μL of the concentrated samples are loaded at low pressure to separate heptameric 6:1 α-HL pore complexes from monomers. After concentration to 5 mL in two consecutive size-exclusion columns, the samples are loaded on Mono S 5/50 GL columns (GE Healthcare; New Jersey, USA). Further FPLC is used to separate the 6:1 α-HL:α-HL-C46 pores from those having different subunit stoichiometries (e.g., 7:0, 5:2). The FPLC mobile phase consists of: A, running buffer: 20 mM 2-(N-morpholino)ethanesulfonic acid (MES), 0.1% Tween®20, at pH 5; B, elution buffer: 2M NaCl, 20 mM MES, 0.1% Tween®20 at pH 5. Purification is performed from 100% A isocratic over 21 minutes followed by a linear gradient of 0-100% B for 20 minutes and then 100% B isocratic over another 2 minutes. The flow rate is 1 ml/min. Pure native 7:0 α-HL heptameric pore complex elutes first and the 6:1 α-HL:α-HL-C46 heptameric pore complex eluted with a retention time of from about 24.5 min to about 25.5 min.

C. DBCO-maleimide reagent reaction of step (a) and isolation of DBCO-modified pore-forming protein of formula (II): Reducing agent TCEP or DTT is removed from the purified 6:1 heptameric α-HL nanopore complex by buffer exchange and the pH of the conjugation buffer adjusted to pH 7. DBCO maleimide reagent (Click Chemistry Tools, A108P-100) is dissolved in anhydrous DMF to a concentration of 100 mM. The maleimide reagent is added in 10 fold excess over the protein and the mixture incubated overnight at 4 C. Excess maleimide reagent is separated from the DBCO-modified nanopore reaction mixture by buffer exchange before the next reaction step.

D. Preparation of azide-modified benzyl thioester cognate click reagent of formula (III): The synthesis of the azide thioester cognate click reagent is carried out using the general reaction scheme shown below.

pared in Step C of this Example. The resulting mixture is allowed to react overnight at 4 C. After 18 hours, the benzyl thioester modified pore protein of formula (IV) is separated from excess unreacted compound by buffer exchange (desalting).

F. Native Chemical Ligation (NCL) reaction resulting in site-specific α-HL-polymerase conjugate of formula (V): A Pol6 DNA polymerase (SEQ ID NO: 9) engineered with an N-terminal cysteine, and the benzyl thioester modified pore protein of formula (IV) prepared in Step E (as a 6:1 nanopore complex), are incubated with the native chemical ligation catalyst, 4-mercaptophenylacetic acid (MPAA) in the relative ratios of 10:1:100 respectively for 18 hours at 4 C. The expected α-HL-polymerase conjugate is characterized by gel electrophoresis and by performing nanopore sequencing experiments as described elsewhere herein Example 2

Site-Selective Conjugation of a Pore-Forming Protein to a Polymerase using Click-Chemistry and SpyCatcher-SpyTag Reaction This example illustrates the use of the site-selective conjugation method of steps (a)-(c) disclosed herein with B and Z reactive groups providing a SpyTag peptide to SpyCatcher protein reaction in step (c). The example demon-

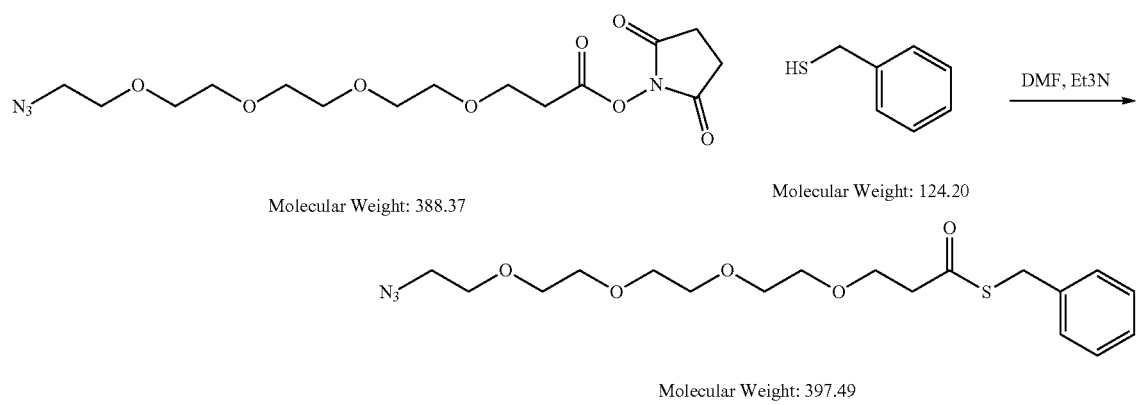

Molecular Weight: 388.37

Molecular Weight: 124.20

Molecular Weight: 397.49

Briefly, solution of azide-PEG$_4$-NHS (0.1 g, 0.00026 mol) in DMF (2 mL) is added dropwise to a solution of benzyl-mercaptan (36 μL, 0.00031 mol, 1.2 eq) in DMF (3 mL) and triethylamine (108 μL, 0.00077 mol, 3 eq) at room temperature. The resulting reaction mixture is stirred at room temperature (RT) and progress of the reaction is monitored by TLC. Upon completion, this reaction mixture is diluted in dichloromethane and washed with NaHCO$_3$ saturated solution, washed with water 2×100 mL, and then dried (Na$_2$SO$_4$). The resulting oil is separated on flash chromatograph (SiO$_2$ in Hexane:EA mixture 10:1) to produce 0.06 g of product (~58%) yield. Mass spectra of the resulting azide-modified benzyl thioester has a major ion at 399 (M+1). Azide-modified benzyl thioester compound is dissolved in DMF to a concentration of 147 mM.

Figure 2:
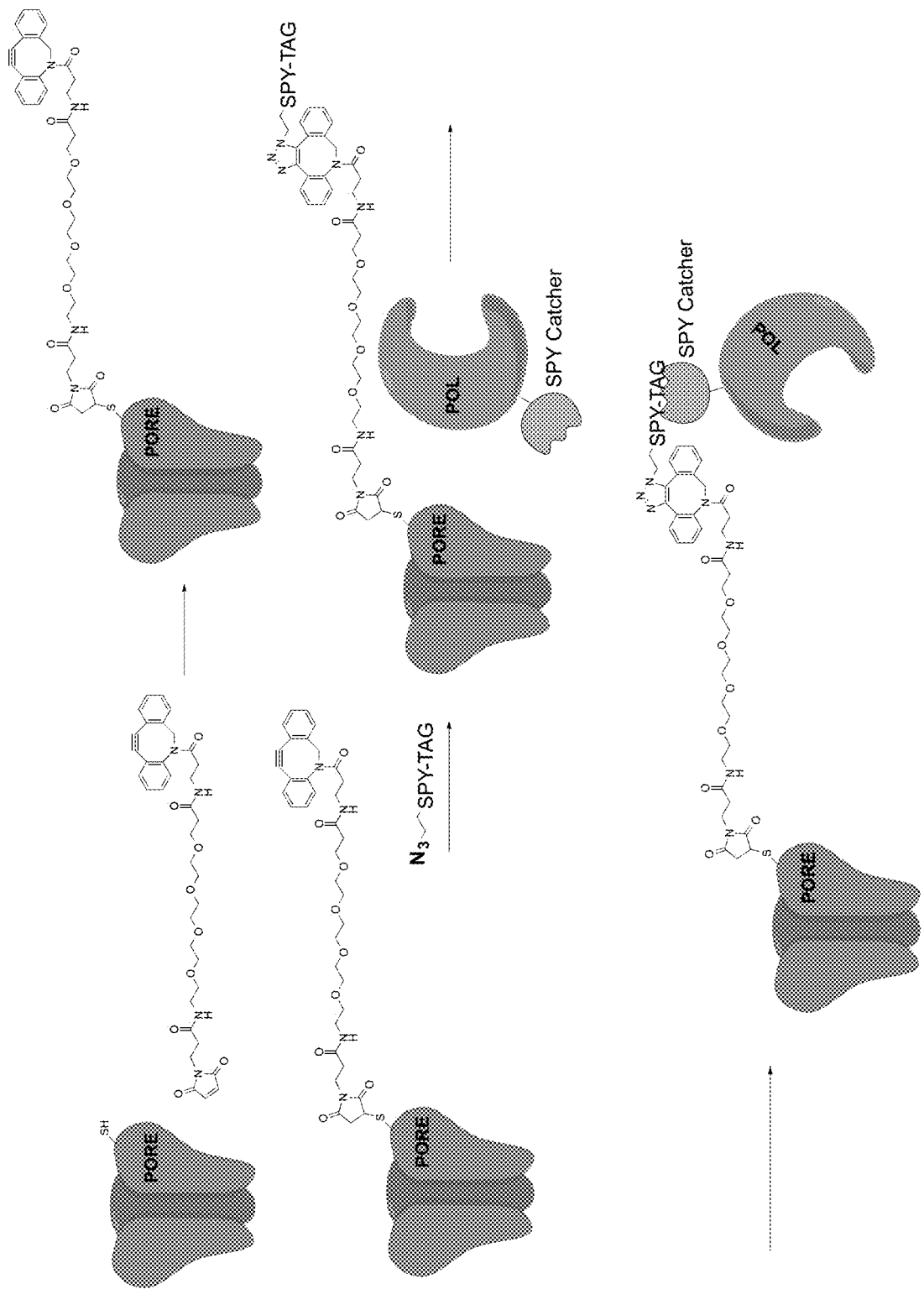
FIG. 2 depicts schematically (from top to bottom) the reaction steps and reagents use in an exemplary method of site-selective conjugation of a polymerase ("POL") to a nanopore ("PORE") via a combination click chemistry and the SpyTag/SpyCatcher reaction in accordance with the methods and compositions of the present disclosure. Exemplary materials and methods useful in the reactions depicted in FIG. 2 are detailed in Example 2 for the particular case of conjugating a α-HL heptameric nanopore complex to a Pol6 DNA polymerase.

E. Click reaction in step (b) of compounds of formula (II) and (III) and isolation/purification of benzyl thioester modified pore-protein of formula (IV): The azide-modified benzyl thioester compound of formula (III) prepared in step D of this Example is added in 10-fold excess to the DBCO-maleimide-modified pore protein nanopore complex prestrates preparation of a composition of formula (V), wherein the SpyTag-modified C46 residue of the α-HL-C46 pore-forming protein, that is part of a heptameric nanopore complex, is site-specifically conjugated to a SpyCatcher-Pol6 DNA polymerase fusion, as is shown schematically in FIG. 2.

Materials and Methods

A. Pore-forming protein (e.g., α-HL) purification: The pore-forming protein monomers used are native α-HL and an engineered α-HL-C46, both encoded with 6-His tags for purification. The K46C (lysine at position 46 substituted with cysteine) mutant of a *S. aureus* α-HL monomer with a 6-His tag ("α-HL-C46") is prepared using standard protein engineering techniques (see e.g., Valeva et al. (2001) and Palmer et al. (1993)). The native α-HL and the α-HL-C46 monomers are recombinantly expressed in *E. coli*, and affinity purified using standard techniques. Briefly, the wild-type α-HL and α-HL-C46 are purified as described in the protocol for "PrepEase" His-tagged protein purification kits (USB-Affymetrix; USA) and exchanged into 1×PBS with 1 mM tris-carboxyethyl-phosphine (TCEP) at pH 7.2 at 1.0 mg/mL protein concentration. All α-HL purification steps are performed in the presence of reducing agent (TCEP or DTT).

B. 6:1 heptameric nanopore formation: Purified α-HL-C46 is mixed with wild-type α-HL in the presence of lipid to form heptamers as follows. To obtain a heptameric pore complex with the optimal 6:1 ratio of native α-HL monomers to the α-HL-C46 mutant monomer, an 11:1 ratio is used for oligomerization. Lipid (1,2-diphytanoyl-sn-glycero-3-phosphocholine, powder, Avanti Polar Lipids) is added to a final concentration of 5 mg/mL in 50 mM tris, 200 mM NaCl, pH 8.0 for 30 minutes at 40° C. 5% octyl-beta-glucoside (β-OG) is added to pop vesicles, as assessed by clearing, to solubilize the proteins. Then samples are concentrated using 100K MWCO filters and spun at 24000 RPM for 30 minutes to pellet the precipitated protein. After equilibrating size-exclusion columns with 30 mM βOG, 75 mM KCl, 20 mM HEPES at pH 7.5, 500 µL of the concentrated samples are loaded at low pressure to separate heptameric 6:1 α-HL pore complexes from monomers. After concentration to 5 mL in two consecutive size-exclusion columns, the samples are loaded on Mono S 5/50 GL columns (GE Healthcare; New Jersey, USA). Further FPLC is used to separate the 6:1 α-HL:α-HL-C46 pores from those having different subunit stoichiometries (e.g., 7:0, 5:2). The FPLC mobile phase consists of: A, running buffer: 20 mM 2-(N-morpholino)ethanesulfonic acid (MES), 0.1% Tween®20, at pH 5; B, elution buffer: 2M NaCl, 20 mM MES, 0.1% Tween®20 at pH 5. Purification is performed from 100% A isocratic over 21 minutes followed by a linear gradient of 0-100% B for 20 minutes and then 100% B isocratic over another 2 minutes. The flow rate is 1 ml/min. Pure native 7:0 α-HL heptameric pore complex elutes first and the 6:1 α-HL:α-HL-C46 heptameric pore complex eluted with a retention time of from about 24.5 min to about 25.5 min.

C. DBCO-maleimide reagent reaction of step (a) and isolation of DBCO-modified pore-forming protein of formula (II): Reducing agent TCEP or DTT is removed from the purified 6:1 heptameric α-HL nanopore complex by buffer exchange and the pH of the conjugation buffer adjusted to pH 7. DBCO maleimide reagent (Click Chemistry Tools, A108P-100) is dissolved in anhydrous DMF to a concentration of 100 mM. The maleimide reagent is added in 10 fold excess over the protein and the mixture incubated overnight at 4 C. Excess maleimide reagent is separated from the DBCO-modified nanopore reaction mixture by buffer exchange before the next reaction step.

D. Preparation of azide-modified SpyTag cognate click reagent of formula (III): The SpyTag peptide amino acid sequence AHIVMVDAYKPTK (SEQ ID NO: 1) with an N-terminal L-azido-homoalanine ("ahA") residue is synthesized and purified using standard automated peptide synthesis methods. The resulting N-azido-modified SpyTag cognate click reagent of formula (III) has the sequence ahA-AHIVMVDAYKPTK (SEQ ID NO: 4). This SpyTag cognate click reagent is dissolved in 20 mM HEPES buffer pH 7.0 ("conjugation buffer") for use in the next step.

E. Conditions for click reaction of compounds of formula (II) and (III) in step (b) and any intermediate isolation or purification of the SpyTag modified pore-protein of formula (IV): A 10-fold excess of the SpyTag cognate click reagent (prepared in Step D) is added to the DBCO-modified pore-forming protein (prepared in Step C). The resulting click reaction mixture is allowed to react overnight at 4 C. After 18 hours, the resulting SpyTag-modified pore protein of formula (IV) is separated from any excess unreacted cognate click reagent by buffer exchange (desalting).

F. Preparation of SpyCatcher-Pol6 polymerase fusion protein: The sequence encoding the Pol6 polymerase of SEQ ID NO: 9 is recombinantly modified such that a sequence encoding the SpyCatcher protein sequence of SEQ ID NO: 8 extends from the N-terminus of the polymerase. The resulting SpyCatcher-Pol6 fusion has the amino acid sequence of SEQ ID NO: 10, which includes an N-terminal His tag for affinity purification and a GGS peptide linker between the Pol6 and the SpyCatcher. The fusion construct is encoded by the nucleotide sequence of SEQ ID NO: 11.

G. SpyCatcher-SpyTag conjugation reaction and isolation of the final product conjugate of α-HL-polymerase of formula (V): The nanopore complex including the SpyTag-modified α-HL pore protein (prepared in Step E) is incubated with the SpyCatcher-Pol6 fusion (prepared in Step F) in a 1 to 4 molar ratio overnight at 4 C. The SpyCatcher protein and SpyTag peptide undergo a spontaneous covalent bond-forming reaction between a lysine residue of the SpyCatcher protein and an aspartic acid residue of the SpyTag peptide. This covalent bond formation results in a specific linkage conjugating the Pol6 polymerase to the α-HL-C46 of the heptameric nanopore complex illustrated generically herein by formula (Vm). Formation of the site-specific conjugate is characterized through gel electrophoresis and through use of the conjugate for nanopore sequencing as described in Example 3.

Example 3

Nanopore Sequencing using an α-HL-Pol6 SpyTag-SpyCatcher Conjugate as Prepared in Example 2 in a Nanopore Array This example illustrates the use of the α-HL-Pol6 nanopore conjugates, prepared as in Example 2, in a nanopore array to sequence a nucleic acid. The α-HL-Pol6 nanopore conjugates are embedded in membranes formed over an array of individually addressable integrated circuit chips. This α-HL-Pol6 nanopore array is exposed to a JAM1A self-priming DNA template and a set of four differently 5'-tagged nucleotide substrates corresponding to the four nucleotides dA, dC, dG, and dT. As the specific 5'-tagged nucleotide that is complementary to the DNA template is captured and bound to the Pol6 polymerase active site, the "tail" of the tag moiety becomes positioned in the α-HL nanopore conjugated nearby. Under the applied AC potential, the presence of the tag in the pore causes a distinctive blocking current compared to the open pore current (i.e., current with no tag in the nanopore). The sequence of blocking currents measured as the Pol6 synthesizes the strand complementary to the template identifies the sequence of DNA template.

Nanopore detection system: The nanopore blocking current measurements are performed using a nanopore array microchip comprising a CMOS microchip that has an array of 128,000 silver electrodes within shallow wells (chip fabricated by Genia Technologies, Mountain View, CA, USA). Methods for fabricating and using such nanopore array microchips can also be found in U.S. Patent Application Publication Nos. 2013/0244340 A1, US 2013/0264207 A1, and US2014/0134616 A1 each of which is hereby incorporated by reference herein. Each well in the array is manufactured using a standard CMOS process with surface modifications that allow for constant contact with biological reagents and conductive salts. Each well can support a phospholipid bilayer membrane with a nanopore-polymerase conjugate embedded therein. The electrode at each well is individually addressable by computer interface. All reagents used are introduced into a simple flow cell above the array microchip using a computer-controlled syringe pump. The chip supports analog to digital conversion and reports electrical measurements from all electrodes independently at a rate of over 1000 points per second. Nanopore blocking current measurements can be made asynchronously at each of 128K addressable nanopore-containing membranes in the array at least once every millisecond (msec) and recorded on the interfaced computer.

Formation of lipid bilayer on chip: The phospholipid bilayer membrane on the chip is prepared using 1,2-diphytanoyl-sn-glycero-3-phosphocholine (Avanti Polar Lipids). The lipid powder is dissolved in decane at 15 mM and then painted in a layer across the wells on the chip. A thinning process then is initiated by pumping air through the cis side of the array wells, thus reducing multi-lamellar lipid membranes to a single bilayer. Bilayer formation is tested using a ramping voltage from 0 to 1000 mV. A typical single bilayer would temporarily open at an applied voltage of between 300 to 500 mV.

Nanopore-polymerase conjugate insertion in membrane: After the lipid bilayer forms on the wells of the array chip, 3 µM of the 5'-tagged nucleotides, 0.1 µM of a 6:1 α-HL-Pol6 nanopore-polymerase conjugate, 0.4 µM of the desired "JAM1A" DNA template, all in a buffer solution of 3 mM $CaCl_2$, 20 mM Hepes, and 500 mM potassium glutamate, pH 8, at 20° C. is added to the cis side of the chip. The nanopore-polymerase conjugate in the mixture spontaneously inserts into the lipid bilayer. Since only $Ca^{2+}$ and no $Mg^{2+}$ metal ion was present, the ternary complex is able to form at the Pol6 active site but the tagged-nucleotide is not incorporated and the 5'-phosphate-linked tag is not released.

The "JAM1A" DNA template is a 99-mer self-priming single-strand that has the sequence 5'-TTTTTGCGCTCGAGATCTCCGTAAGGAGATCT-CGAGCGCGGGACTACTACTGGGATCATCATAGC-CACCTCAGCTGCACGTAAGTGCAGCTGAGGTGGC-3' (SEQ ID NO:12). This DNA template has a first available position on the template for binding to a complementary dT nucleotide.

In the present example, the four tagged nucleotides used as polymerase substrates in the mixture were: dA6P-Cy3-T4-(idSp-T)4-T18-C3 (SEQ ID NO:13), dC6P-Cy3-T30-C3 (SEQ ID NO:14), dT6P-Cy3-dT4(N3-CE-dT)3-dT23-C3 (SEQ ID NO:15), dG6P-T6-Tmp6-T19-C3 (SEQ ID NO:16). However, a wide range of 5'-tagged nucleotides useful for nanopore devices are available, such as those described in WO 2015/148402, published Oct. 1, 2015, which is hereby incorporated by reference herein for all purposes.

Nanopore blocking current measurements: The buffer solution used as the electrolyte solution for the nanopore current blockade measurements is 500 mM potassium glutamate, pH 8, 3 mM $MgCl_2$, 20 mM Hepes, 5mM TCEP, at 20° C. A Pt/Ag/AgCl electrode setup is used and an AC current of a −10 mV to 200 mV square waveform applied. AC current can have certain advantages for nanopore detection as it allows for the tag to be repeatedly directed into and then expelled from the nanopore thereby providing more opportunities to detection. AC current also can provide a steadier potential for a more stable current signal and less degradation of the electrodes over time.

Signals representing four distinct current blockade events were observed from the four different 5'-tagged nucleotides as they were captured by the α-HL-Pol6 nanopore-polymerase conjugates primed with the JAM1A DNA template. Plots recorded of the blocking current events were analyzed. Events that last longer than 10 ms and that reduced the open channel current from 0.8 to 0.2 were deemed to indicate productive nucleotide capture by the α-HL-Pol6 nanopore-polymerase conjugate. In three different experiments, the JAM1A DNA sequence was called correctly at rates of 45%, 48%, and 73%, with very low mismatch calls but several regions of incorrect insertion calls. These results indicate that the methods of the present disclosure can provide α-HL-Pol6 nanopore-polymerase conjugates capable of detecting and/or sequencing specific DNA using a nanopore device. Further optimization of array conditions can result in higher correct sequence call rates.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The invention claimed is:

1. A composition comprising a conjugate of a protein and a biomolecule of formula (Vh) or (Vi):

(Vh)

(Vi)

wherein,
n=1 to 50, and q, r, and s each independently=0, 1, 2, or 3;
$L_B$ is a linker;
B is a SpyTaq peptide;
and wherein the protein contains a thiol group
Z is a SpyCatcher protein.

2. The composition of claim 1, wherein the SpyTag peptide and SpyCatcher protein each comprise a fragment of an amino acid sequence of the CnaB2 domain from the *Streptococcus pyogenes* fibronectin binding protein FbaB.

3. The composition of claim 1, wherein the protein is a pore-forming protein, optionally selected from the group consisting of α-hemolysin, β-hemolysin, γ-hemolysin, aerolysin, cytolysin, leukocidin, melittin, MspA porin and porin A.

4. The composition of claim 1, wherein the protein is a pore-forming protein embedded in a membrane.

5. The composition of claim 1, wherein the biomolecule is an enzyme capable of catalyzing the synthesis of a polymer, selected from the group consisting of a DNA polymerase, RNA polymerase, reverse transcriptase, and DNA ligase.

6. The composition of claim 1, wherein the conjugate of formula (Vh) comprises a compound of formula (Vk):

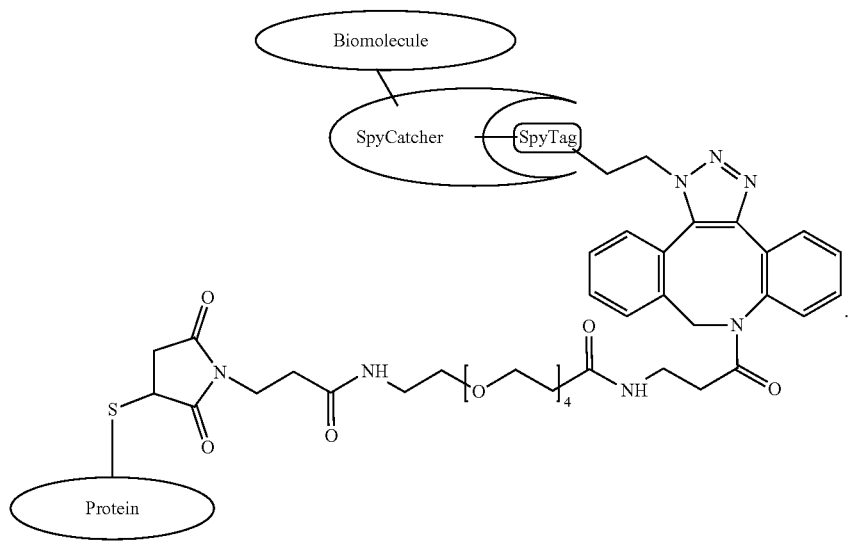
(Vk)
7. The composition of claim 6, wherein the protein is α-hemolysin and the biomolecule is DNA polymerase.
8. The composition of claim 1, wherein the conjugate of formula (Vi) comprises a compound of formula (Vm):
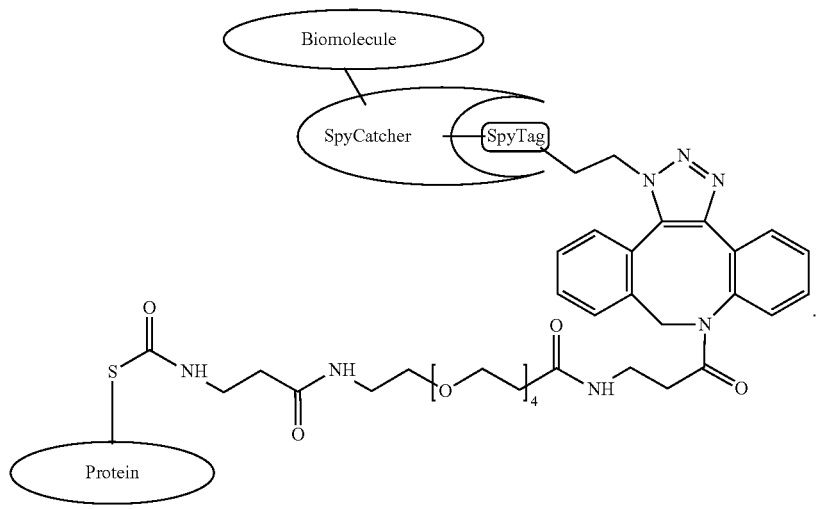
(Vm)
9. The composition of claim 8, wherein the protein is α-hemolysin and the biomolecule is DNA polymerase.
* * * * *

SEQUENCE LISTING

```
<160> NUMBER OF SEQ ID NOS: 16

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Ala His Ile Val Met Val Asp Ala Tyr Lys Pro Thr Lys
1               5                   10

<210> SEQ ID NO 2
<211> LENGTH: 10
<212> TYPE: PRT
<213> ORGANISM: Artificial sequence
<220> FEATURE:
```

```
<223> OTHER INFORMATION: Synthetic peptide

<400> SEQUENCE: 2

Ala His Ile Val Met Val Asp Ala Tyr Lys
1               5                   10

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Ala His Ile Val Met Val Asp Ala
1               5

<210> SEQ ID NO 4
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is 2-aminobutyric acid

<400> SEQUENCE: 4

Xaa Ala His Ile Val Met Val Asp Ala Tyr Lys Pro Thr Lys
1               5                   10

<210> SEQ ID NO 5
<211> LENGTH: 143
<212> TYPE: PRT
<213> ORGANISM: Artificial sequence
<220> FEATURE:
<223> OTHER INFORMATION: 143 aa fragment of CnaB2 domain of the
      Streptococcus pycogenes fibronectin binding protein, FbaB

<400> SEQUENCE: 5

Ser Tyr Tyr His His His His His Asp Tyr Asp Ile Pro Thr Thr
1               5                   10                  15

Glu Asn Leu Tyr Phe Gln Gly Ala Met Val Asp Thr Leu Ser Gly Leu
                20                  25                  30

Ser Ser Glu Gln Gly Gln Ser Gly Asp Met Thr Ile Glu Glu Asp Ser
            35                  40                  45

Ala Thr His Ile Lys Phe Ser Lys Arg Asp Glu Asp Gly Lys Glu Leu
        50                  55                  60

Ala Gly Ala Thr Met Glu Leu Arg Asp Ser Ser Gly Lys Thr Ile Ser
65                  70                  75                  80

Thr Trp Ile Ser Asp Gly Gln Val Lys Asp Phe Tyr Leu Tyr Pro Gly
                85                  90                  95

Lys Tyr Thr Phe Val Glu Thr Ala Ala Pro Asp Gly Tyr Glu Val Ala
            100                 105                 110

Thr Ala Ile Thr Phe Thr Val Asn Glu Gln Gly Gln Val Thr Val Asn
        115                 120                 125

Gly Lys Ala Thr Lys Gly Asp Ala His Ile Val Met Val Asp Ala
    130                 135                 140

<210> SEQ ID NO 6
<211> LENGTH: 129
<212> TYPE: PRT
```

<213> ORGANISM: Artificial Sequence
<220> FEATURE:
<223> OTHER INFORMATION: 129 aa N-terminal CnaB2 domain sequence
      fragment of the Streptococcus pycogenes fibronectin binding
      protein, FbaB

<400> SEQUENCE: 6

```
Asp Tyr Asp Ile Pro Thr Thr Glu Asn Leu Tyr Phe Gln Gly Ala Met
1               5                   10                  15

Val Asp Thr Leu Ser Gly Leu Ser Ser Glu Gln Gly Gln Ser Gly Asp
            20                  25                  30

Met Thr Ile Glu Glu Asp Ser Ala Thr His Ile Lys Phe Ser Lys Arg
        35                  40                  45

Asp Glu Asp Gly Lys Glu Leu Ala Gly Ala Thr Met Glu Leu Arg Asp
    50                  55                  60

Ser Ser Gly Lys Thr Ile Ser Thr Trp Ile Ser Asp Gly Gln Val Lys
65                  70                  75                  80

Asp Phe Tyr Leu Tyr Pro Gly Lys Tyr Thr Phe Val Glu Thr Ala Ala
                85                  90                  95

Pro Asp Gly Tyr Glu Val Ala Thr Ala Ile Thr Phe Thr Val Asn Glu
            100                 105                 110

Gln Gly Gln Val Thr Val Asn Gly Lys Ala Thr Lys Gly Asp Ala His
        115                 120                 125

Ile
```

<210> SEQ ID NO 7
<211> LENGTH: 138
<212> TYPE: PRT
<213> ORGANISM: Artificial Sequence
<220> FEATURE:
<223> OTHER INFORMATION: 138 aa N-terminal CnaB2 domain sequence
      fragment of the Streptococcus pycogenes fibronectin binding
      protein, FbaB

<400> SEQUENCE: 7

```
Ser Tyr Tyr His His His His His His Asp Tyr Asp Ile Pro Thr Thr
1               5                   10                  15

Glu Asn Leu Tyr Phe Gln Gly Ala Met Val Asp Thr Leu Ser Gly Leu
            20                  25                  30

Ser Ser Glu Gln Gly Gln Ser Gly Asp Met Thr Ile Glu Glu Asp Ser
        35                  40                  45

Ala Thr His Ile Lys Phe Ser Lys Arg Asp Glu Asp Gly Lys Glu Leu
    50                  55                  60

Ala Gly Ala Thr Met Glu Leu Arg Asp Ser Ser Gly Lys Thr Ile Ser
65                  70                  75                  80

Thr Trp Ile Ser Asp Gly Gln Val Lys Asp Phe Tyr Leu Tyr Pro Gly
                85                  90                  95

Lys Tyr Thr Phe Val Glu Thr Ala Ala Pro Asp Gly Tyr Glu Val Ala
            100                 105                 110

Thr Ala Ile Thr Phe Thr Val Asn Glu Gln Gly Gln Val Thr Val Asn
        115                 120                 125

Gly Lys Ala Thr Lys Gly Asp Ala His Ile
    130                 135
```

<210> SEQ ID NO 8
<211> LENGTH: 143
<212> TYPE: PRT
<213> ORGANISM: Artificial Sequence
<220> FEATURE:

<223> OTHER INFORMATION: Fusion of fragment of CnaB2 domain of the
Streptococcus pyogenes fibronectin binding protein, FbaB with
N-terminal His tag and C-terminal GGS linker

<400> SEQUENCE: 8

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
        35                  40                  45

Asp Ser Ala Thr His Ile Lys Phe Ser Lys Arg Asp Glu Asp Gly Lys
    50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
        115                 120                 125

Val Asn Gly Lys Ala Thr Lys Gly Asp Ala His Ile Gly Gly Ser
    130                 135                 140

<210> SEQ ID NO 9
<211> LENGTH: 726
<212> TYPE: PRT
<213> ORGANISM: Clostridium phage phiCPV4

<400> SEQUENCE: 9

Asp Lys His Thr Gln Tyr Val Lys Glu His Ser Phe Asn Tyr Asp Glu
1               5                   10                  15

Tyr Lys Lys Ala Asn Phe Asp Lys Ile Glu Cys Leu Ile Phe Asp Thr
            20                  25                  30

Glu Ser Cys Thr Asn Tyr Glu Asn Asp Asn Thr Gly Ala Arg Val Tyr
        35                  40                  45

Gly Trp Gly Leu Gly Val Thr Arg Asn His Asn Met Ile Tyr Gly Gln
    50                  55                  60

Asn Leu Asn Gln Phe Trp Glu Val Cys Gln Asn Ile Phe Asn Asp Trp
65                  70                  75                  80

Tyr His Asp Asn Lys His Thr Ile Lys Ile Thr Lys Thr Lys Lys Gly
                85                  90                  95

Phe Pro Lys Arg Lys Tyr Ile Lys Phe Pro Ile Ala Val His Asn Leu
            100                 105                 110

Gly Trp Asp Val Glu Phe Leu Lys Tyr Ser Leu Val Glu Asn Gly Phe
        115                 120                 125

Asn Tyr Asp Lys Gly Leu Leu Lys Thr Val Phe Ser Lys Gly Ala Pro
    130                 135                 140

Tyr Gln Thr Val Thr Asp Val Glu Glu Pro Lys Thr Phe His Ile Val
145                 150                 155                 160

Gln Asn Asn Asn Ile Val Tyr Gly Cys Asn Val Tyr Met Asp Lys Phe
                165                 170                 175

Phe Glu Val Glu Asn Lys Asp Gly Ser Thr Thr Glu Ile Gly Leu Cys
            180                 185                 190

Leu Asp Phe Phe Asp Ser Tyr Lys Ile Ile Thr Cys Ala Glu Ser Gln
        195                 200                 205

```
Phe His Asn Tyr Val His Asp Val Asp Pro Met Phe Tyr Lys Met Gly
    210                 215                 220

Glu Glu Tyr Asp Tyr Asp Thr Trp Arg Ser Pro Thr His Lys Gln Thr
225                 230                 235                 240

Thr Leu Glu Leu Arg Tyr Gln Tyr Asn Asp Ile Tyr Met Leu Arg Glu
                245                 250                 255

Val Ile Glu Gln Phe Tyr Ile Asp Gly Leu Cys Gly Gly Glu Leu Pro
                260                 265                 270

Leu Thr Gly Met Arg Thr Ala Ser Ser Ile Ala Phe Asn Val Leu Lys
            275                 280                 285

Lys Met Thr Phe Gly Glu Glu Lys Thr Glu Gly Tyr Ile Asn Tyr
290                 295                 300

Phe Glu Leu Asp Lys Lys Thr Lys Phe Glu Phe Leu Arg Lys Arg Ile
305                 310                 315                 320

Glu Met Glu Ser Tyr Thr Gly Gly Tyr Thr His Ala Asn His Lys Ala
                325                 330                 335

Val Gly Lys Thr Ile Asn Lys Ile Gly Cys Ser Leu Asp Ile Asn Ser
                340                 345                 350

Ser Tyr Pro Ser Gln Met Ala Tyr Lys Val Phe Pro Tyr Gly Lys Pro
            355                 360                 365

Val Arg Lys Thr Trp Gly Arg Lys Pro Lys Thr Glu Lys Asn Glu Val
    370                 375                 380

Tyr Leu Ile Glu Val Gly Phe Asp Phe Val Glu Pro Lys His Glu Glu
385                 390                 395                 400

Tyr Ala Leu Asp Ile Phe Lys Ile Gly Ala Val Asn Ser Lys Ala Leu
                405                 410                 415

Ser Pro Ile Thr Gly Ala Val Ser Gly Gln Glu Tyr Phe Cys Thr Asn
            420                 425                 430

Ile Lys Asp Gly Lys Ala Ile Pro Val Tyr Lys Glu Leu Lys Asp Thr
        435                 440                 445

Lys Leu Thr Thr Asn Tyr Asn Val Val Leu Thr Ser Val Glu Tyr Glu
450                 455                 460

Phe Trp Ile Lys His Phe Asn Phe Gly Val Phe Lys Lys Asp Glu Tyr
465                 470                 475                 480

Asp Cys Phe Glu Val Asp Asn Leu Glu Phe Thr Gly Leu Lys Ile Gly
                485                 490                 495

Ser Ile Leu Tyr Tyr Lys Ala Glu Lys Gly Lys Phe Lys Pro Tyr Val
            500                 505                 510

Asp His Phe Thr Lys Met Lys Val Glu Asn Lys Lys Leu Gly Asn Lys
        515                 520                 525

Pro Leu Thr Asn Gln Ala Lys Leu Ile Leu Asn Gly Ala Tyr Gly Lys
530                 535                 540

Phe Gly Thr Lys Gln Asn Lys Glu Glu Lys Asp Leu Ile Met Asp Lys
545                 550                 555                 560

Asn Gly Leu Leu Thr Phe Thr Gly Ser Val Thr Glu Tyr Glu Gly Lys
                565                 570                 575

Glu Phe Tyr Arg Pro Tyr Ala Ser Phe Val Thr Ala Tyr Gly Arg Leu
            580                 585                 590

Gln Leu Trp Asn Ala Ile Ile Tyr Ala Val Gly Val Glu Asn Phe Leu
        595                 600                 605

Tyr Cys Asp Thr Asp Ser Ile Tyr Cys Asn Arg Glu Val Asn Ser Leu
610                 615                 620
```

```
Ile Glu Asp Met Asn Ala Ile Gly Glu Thr Ile Asp Lys Thr Ile Leu
625                 630                 635                 640

Gly Lys Trp Asp Val Glu His Val Phe Asp Lys Phe Lys Val Leu Gly
                645                 650                 655

Gln Lys Lys Tyr Met Tyr His Asp Cys Lys Glu Asp Lys Thr Asp Leu
            660                 665                 670

Lys Cys Cys Gly Leu Pro Ser Asp Ala Arg Lys Ile Ile Ile Gly Gln
        675                 680                 685

Gly Phe Asp Glu Phe Tyr Leu Gly Lys Asn Val Glu Gly Lys Lys Gln
    690                 695                 700

Arg Lys Lys Val Ile Gly Gly Cys Leu Leu Leu Asp Thr Leu Phe Thr
705                 710                 715                 720

Ile Lys Lys Ile Met Phe
                725

<210> SEQ ID NO 10
<211> LENGTH: 869
<212> TYPE: PRT
<213> ORGANISM: Artificial sequence
<220> FEATURE:
<223> OTHER INFORMATION: Synthetic fusion protein (Pol6-SpyCatcher)

<400> SEQUENCE: 10

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
                20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
        50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
                100                 105                 110

Val Ala Thr Ala Ile Thr Phe Thr Val Asn Glu Gln Gly Gln Val Thr
            115                 120                 125

Val Asn Gly Lys Ala Thr Lys Gly Asp Ala His Ile Gly Gly Ser Asp
130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Asp Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
        195                 200                 205

Leu Asn Gln Phe Trp Glu Val Cys Gln Asn Ile Phe Asn Asp Trp Tyr
    210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255
```

```
Trp Asp Val Glu Phe Leu Lys Tyr Ser Leu Val Glu Asn Gly Phe Asn
            260                 265                 270

Tyr Asp Lys Gly Leu Leu Lys Thr Val Phe Ser Lys Gly Ala Pro Tyr
        275                 280                 285

Gln Thr Val Thr Asp Val Glu Glu Pro Lys Thr Phe His Ile Val Gln
    290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
            340                 345                 350

His Asn Tyr Val His Asp Val Asp Pro Met Phe Tyr Lys Met Gly Glu
        355                 360                 365

Glu Tyr Asp Tyr Asp Thr Trp Arg Ser Pro Thr His Lys Gln Thr Thr
    370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
        435                 440                 445

Glu Leu Asp Lys Lys Thr Lys Phe Glu Phe Leu Arg Lys Arg Ile Glu
    450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ser
                485                 490                 495

Tyr Pro Ser Gln Met Ala Tyr Lys Val Phe Pro Tyr Gly Lys Pro Val
            500                 505                 510

Arg Lys Thr Trp Gly Arg Lys Pro Lys Thr Glu Lys Asn Glu Val Tyr
        515                 520                 525

Leu Ile Glu Val Gly Phe Asp Phe Val Glu Pro Lys His Glu Glu Tyr
    530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
            580                 585                 590

Leu Thr Thr Asn Tyr Asn Val Val Leu Thr Ser Val Glu Tyr Glu Phe
        595                 600                 605

Trp Ile Lys His Phe Asn Phe Gly Val Phe Lys Lys Asp Glu Tyr Asp
    610                 615                 620

Cys Phe Glu Val Asp Asn Leu Glu Phe Thr Gly Leu Lys Ile Gly Ser
625                 630                 635                 640
```

```
Ile Leu Tyr Tyr Lys Ala Glu Lys Gly Lys Phe Lys Pro Tyr Val Asp
                645                 650                 655

His Phe Thr Lys Met Lys Val Glu Asn Lys Lys Leu Gly Asn Lys Pro
            660                 665                 670

Leu Thr Asn Gln Ala Lys Leu Ile Leu Asn Gly Ala Tyr Gly Lys Phe
        675                 680                 685

Gly Thr Lys Gln Asn Lys Glu Glu Lys Asp Leu Ile Met Asp Lys Asn
    690                 695                 700

Gly Leu Leu Thr Phe Thr Gly Ser Val Thr Glu Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
        755                 760                 765

Glu Asp Met Asn Ala Ile Gly Glu Thr Ile Asp Lys Thr Ile Leu Gly
    770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Gly Gln Gly
            820                 825                 830

Phe Asp Glu Phe Tyr Leu Gly Lys Asn Val Glu Gly Lys Lys Gln Arg
        835                 840                 845

Lys Lys Val Ile Gly Gly Cys Leu Leu Leu Asp Thr Leu Phe Thr Ile
    850                 855                 860

Lys Lys Ile Met Phe
865

<210> SEQ ID NO 11
<211> LENGTH: 2610
<212> TYPE: DNA
<213> ORGANISM: Artificial sequence
<220> FEATURE:
<223> OTHER INFORMATION: Synthetic nucleotide sequence encoding
      Pol6-SpyCatcher fusion protein

<400> SEQUENCE: 11
atgcatcacc atcatcatca ccaccacagc ggtgactacg acatcccgac caccgagaac      60
ctgtacttcc agggcgccat ggtggacaca ctgagcggtc tgagcagtga acagggccag     120
agcggcgaca tgaccattga gaggacagc gccacccaca tcaagttcag caagcgtgac     180
gaggacggta aggaactggc cggcgccacc atggaactgc gtgacagcag cggcaagacc     240
atcagcacct ggatcagcga tggccaggtg aaggacttct acctgtaccc gggcaagtac     300
accttcgtgg agacagccgc accggacggt tacgaggttg ccaccgccat caccttcacc     360
gtgaacgagc agggccaagt gaccgttaac ggcaaggcca ccaagggtga cgcccacatc     420
ggcggttccg acaaacacac gcagtacgtc aaagagcata gcttcaatta tgacgagtat     480
aagaaagcga atttcgacaa gatcgagtgc ctgatctttg acaccgagag ctgcacgaat     540
```

```
tatgagaacg ataataccgg tgcacgtgtt tacggttggg gtcttggcgt cacccgcaac    600
cacaatatga tctacggcca aaatctgaat cagttttggg aagtatgcca gaacattttc    660
aatgattggt atcacgacaa caaacatacc attaagatta ccaagaccaa gaaaggcttc    720
ccgaaacgta agtacattaa gtttccgatt gcagttcaca atttgggctg ggatgttgaa    780
ttcctgaagt atagcctggt ggagaatggt ttcaattacg acaagggtct gctgaaaact    840
gttttagca agggtgcgcc gtaccaaacc gtgaccgatg ttgaggaacc gaaaacgttc    900
catatcgtcc agaataacaa catcgtttat ggttgtaacg tgtatatgga caaattcttt    960
gaggtcgaga caaagacgg ctctaccacc gagattggcc tgtgcttgga tttcttcgat   1020
agctataaga tcatcacgtg tgctgagagc cagttccaca attacgttca tgatgtggat   1080
ccaatgttct acaaaatggg tgaagagtat gattacgata cttggcgtag cccgacgcac   1140
aagcagacca ccctggagct gcgctaccaa tacaatgata tctatatgct gcgtgaagtc   1200
atcgaacagt tttacattga cggtttatgt ggcggcgagc tgccgctgac cggcatgcgc   1260
accgcttcca gcattgcgtt caacgtgctg aaaaagatga cctttggtga ggaaaagacg   1320
gaagagggct acatcaacta ttttgaattg gacaagaaaa ccaaattcga gtttctgcgt   1380
aagcgcattg aaatggaatc gtacaccggt ggctatacgc acgcaaatca caaagccgtt   1440
ggtaagacta ttaacaagat cggttgctct ttggacatta acagctcata cccttcgcag   1500
atggcgtaca aggtctttcc gtatggcaaa ccggttcgta agacctgggg tcgtaaacca   1560
aagaccgaga gaacgaagt ttatctgatt gaagttggct ttgacttcgt ggagccgaaa   1620
cacgaagaat acgcgctgga tatctttaag attggtgcgg tgaactctaa agcgctgagc   1680
ccgatcaccg gcgctgtcag cggtcaagag tatttctgta cgaacattaa agacggcaaa   1740
gcaatcccgg tttacaaaga actgaaggac accaaattga ccactaacta caatgtcgtg   1800
ctgaccagcg tggagtacga gttctggatc aaacacttca attttggtgt gtttaagaaa   1860
gacgagtacg actgtttcga agttgacaat ctggagttta cgggtctgaa gattggttcc   1920
attctgtact acaaggcaga gaaaggcaag tttaaaccctt acgtggatca cttcacgaaa   1980
atgaaagtgg agaacaagaa actgggtaat aagccgctga cgaatcaggc aaagctgatt   2040
ctgaacggtg cgtacggcaa attcggcacc aaacaaaaca aagaagagaa agatttgatc   2100
atggataaga acggtttgct gaccttcacg ggtagcgtca cggaatacga gggtaaagaa   2160
ttctatcgtc cgtatgcgag cttcgttact gcctatggtc gcctgcaact gtggaacgcg   2220
attatctacg cggttggtgt ggagaatttt ctgtactgcg acaccgacag catctattgt   2280
aaccgtgaag ttaacagcct cattgaggat atgaacgcca ttggtgaaac catcgataaa   2340
acgattctgg gtaaatggga cgtggagcat gtctttgata agtttaaggt cctgggccag   2400
aagaagtaca tgtatcatga ttgcaaagaa gataaaacgg acctgaagtg ttgcggtctg   2460
ccgagcgatg cccgtaagat tatcattggt caaggtttcg acgagtttta tctgggcaaa   2520
aatgtcgaag gtaagaagca acgcaaaaaa gtgatcggcg gttgcctgct gctggacacc   2580
ctgtttacga tcaagaaaat catgttctaa                                    2610
```

<210> SEQ ID NO 12
<211> LENGTH: 99
<212> TYPE: DNA
<213> ORGANISM: Artificial sequence
<220> FEATURE:
<223> OTHER INFORMATION: Self-priming DNA template sequence

<400> SEQUENCE: 12 ttttttgcgct cgagatctcc gtaaggagat ctcgagcgcg ggactactac tgggatcatc    60
atagccacct cagctgcacg taagtgcagc tgaggtggc                            99

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide tag
<220> FEATURE:
<221> NAME/KEY: misc_feature
<222> LOCATION: (1)..(1)
<223> OTHER INFORMATION: 5'-cyanine3-phosphate-dT
<220> FEATURE:
<221> NAME/KEY: misc_feature
<222> LOCATION: (5)..(5)
<223> OTHER INFORMATION: furan amidite
<220> FEATURE:
<221> NAME/KEY: misc_feature
<222> LOCATION: (7)..(7)
<223> OTHER INFORMATION: furan amidite
<220> FEATURE:
<221> NAME/KEY: misc_feature
<222> LOCATION: (9)..(9)
<223> OTHER INFORMATION: furan amidite
<220> FEATURE:
<221> NAME/KEY: misc_feature
<222> LOCATION: (11)..(11)
<223> OTHER INFORMATION: furan amidite
<220> FEATURE:
<221> NAME/KEY: misc_feature
<222> LOCATION: (30)..(30)
<223> OTHER INFORMATION: 3'-propanol-dT

<400> SEQUENCE: 13
ttttntntnt nttttttttt tttttttttt                                      30

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide tag
<220> FEATURE:
<221> NAME/KEY: misc_feature
<222> LOCATION: (1)..(1)
<223> OTHER INFORMATION: 5'-cyanine3-phosphate-dT
<220> FEATURE:
<221> NAME/KEY: misc_feature
<222> LOCATION: (30)..(30)
<223> OTHER INFORMATION: 3'-propanol-dT

<400> SEQUENCE: 14
tttttttttt tttttttttt tttttttttt                                      30

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide tag
<220> FEATURE:
<221> NAME/KEY: misc_feature
<222> LOCATION: (1)..(1)
<223> OTHER INFORMATION: 5'-cyanine3-phosphate-dT
<220> FEATURE:

```
<221> NAME/KEY: misc_feature
<222> LOCATION: (5)..(7)
<223> OTHER INFORMATION: N3-cyanoethyl-dT
<220> FEATURE:
<221> NAME/KEY: misc_feature
<222> LOCATION: (30)..(30)
<223> OTHER INFORMATION: 3'-propanol-dT

<400> SEQUENCE: 15
ttttnnnttt tttttttttt tttttttttt                                   30

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide tag
<220> FEATURE:
<221> NAME/KEY: misc_feature
<222> LOCATION: (7)..(12)
<223> OTHER INFORMATION: thymidine methylphosphonate
<220> FEATURE:
<221> NAME/KEY: misc_feature
<222> LOCATION: (31)..(31)
<223> OTHER INFORMATION: 3'-propanol-dT

<400> SEQUENCE: 16 tttttnnnn nntttttttt tttttttttt t                                  31
```